US012569573B2

(12) United States Patent
Srivastava et al.

(10) Patent No.: US 12,569,573 B2
(45) Date of Patent: Mar. 10, 2026

(54) ENHANCED TRANSDUCTION OF AAV VECTORS ENCODING MICRORNAS

(71) Applicant: University of Florida Research Foundation, Incorporated, Gainesville, FL (US)

(72) Inventors: Arun Srivastava, Gainesville, FL (US); Keyun Qing, Newberry, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1020 days.

(21) Appl. No.: 17/603,300

(22) PCT Filed: Apr. 13, 2020

(86) PCT No.: PCT/US2020/027927
§ 371 (c)(1),
(2) Date: Oct. 12, 2021

(87) PCT Pub. No.: WO2020/214526
PCT Pub. Date: Oct. 22, 2020

(65) Prior Publication Data
US 2022/0273815 A1 Sep. 1, 2022

Related U.S. Application Data

(60) Provisional application No. 62/833,662, filed on Apr. 13, 2019.

(51) Int. Cl.
*A61K 48/00* (2006.01)
*A61K 45/06* (2006.01)
*C12N 15/113* (2010.01)
*C12N 15/86* (2006.01)

(52) U.S. Cl.
CPC ............ *A61K 48/005* (2013.01); *A61K 45/06* (2013.01); *C12N 15/113* (2013.01); *C12N 15/86* (2013.01); *C12N 2310/141* (2013.01); *C12N 2750/14122* (2013.01); *C12N 2750/14123* (2013.01); *C12N 2750/14142* (2013.01); *C12N 2800/40* (2013.01)

(58) Field of Classification Search
CPC ................ C12N 2310/141; C12N 2750/14143
See application file for complete search history.

(56) References Cited

U.S. PATENT DOCUMENTS

| | | | |
|---|---|---|---|
| 2006/0134639 A1* | 6/2006 | Huffel | C12N 15/63 435/6.14 |
| 2009/0136957 A1* | 5/2009 | Ivanovska | C12N 15/113 435/6.12 |
| 2014/0219964 A1 | 8/2014 | Wang et al. | |
| 2016/0251656 A1 | 9/2016 | Berriel Diaz et al. | |

FOREIGN PATENT DOCUMENTS

| | | | | |
|---|---|---|---|---|
| WO | WO 2014/125101 A1 | 8/2014 | | |
| WO | WO-2016081927 A2 * | 5/2016 | ............ | C12N 15/86 |
| WO | WO-2017075335 A1 * | 5/2017 | ............ | A61K 35/76 |

OTHER PUBLICATIONS

Mah C, Qing K, Khuntirat B, Ponnazhagan S, Wang XS, Kube DM, Yoder MC, Srivastava A. Adeno-associated virus type 2-mediated gene transfer: role of epidermal growth factor receptor protein tyrosine kinase in transgene expression. J Virol. Dec. 1998; 72(12):9835-43. (Year: 1998).*
Yue J, Sheng Y, Orwig KE. Identification of novel homologous microRNA genes in the rhesus macaque genome. BMC Genomics. Jan. 10, 2008;9:8. doi: 10.1186/1471-2164-9-8. PMID: 18186931; PMCID: PMC2254598. (Year: 2008).*
Invitation to Pay Additional Feed for International Application No. PCT/US2020/027927 mailed Jul. 27, 2020.
International Search Report and Written Opinion for International Application No. PCT/US2020/027927 mailed Sep. 28, 2020.
International Preliminary Report on Patentability for International Application No. PCT/US2020/027927 mailed Oct. 28, 2021.
Clayton et al., The role of microRNAs in glucocorticoid action. J Biol Chem. Feb. 9, 2018;293(6):1865-1874. doi: 10.1074/jbc.R117. 000366. Epub Jan. 4, 2018.
GenBank Accession No. DQ642634.1, Bos taurus microRNA bta-miR-17-5p, complete sequence, Jun. 26, 2006 [online]. Retrieved from the internet: https://www.ncbi.nlm.nih gov/nuccore/DQ642634. 1.
Gruszka et al., The Oncogenic Relevance of miR-17-92 Cluster and Its Paralogous miR-06b-25 and miR-106a-363 Clusters in Brain Tumors. Int J Mol Sci. Mar. 16, 2018;19(3):879. doi: 10.3390/ ijms19030879.
Jin et al., miR-17-92 Cluster Regulates Adult Hippocampal Neurogenesis, Anxiety, and Depression. Cell Rep. Aug. 9, 2016;16(6):1653-1663. doi: 10.1016/j.celrep.2016.06.101. Epub Jul. 28, 2016.
Kay et al., Targeting photoreceptors via intravitreal delivery using novel, capsid-mutated AAV vectors. PLoS One. Apr. 26, 2013;8(4):e62097. doi: 10.1371/journal.pone.0062097. Erratum in: PLoS One. 2013;8(9). doi:10.1371/annotation/99ee1789-a658-4fb0-8593-40a40e9f344a.

(Continued)

*Primary Examiner* — Fereydoun G Sajjadi
*Assistant Examiner* — Qinhua Gu
(74) *Attorney, Agent, or Firm* — Wolf, Greenfield & Sacks, P.C.

(57) ABSTRACT

Provided herein are recombinant adeno-associated virus (rAAV) particles encoding microRNAs targeting the glucocorticoid receptor (GR) pathway, and in particular a microRNA17-92 (miR 17-92) cluster, and genes of interest. The modified genomes of these rAAV particles comprise heterologous nucleic acid sequences encoding microRNA structures. These particles exhibit enhanced transduction efficiencies in mammalian cells. Also provided herein are compositions of nucleic acids encoding the miR 17-92 cluster and nucleic acids encoding a gene of interest. Further provided herein are methods for administering these nucleic acid compositions to enhance transduction efficiencies.

11 Claims, 12 Drawing Sheets

Specification includes a Sequence Listing.

(56) References Cited

OTHER PUBLICATIONS

Mogilyansky et al., The miR-17/92 cluster: a comprehensive update on its genomics, genetics, functions and increasingly important and numerous roles in health and disease. Cell Death Differ. Dec. 2013;20(12):1603-14. doi: 10.1038/cdd.2013.125.

Tasfaout et al., Split intein-mediated protein trans-splicing to express large dystrophins. Nature. Aug. 2024;632(8023):192-200. doi: 10.1038/s41586-024-07710-8. Epub Jul. 17, 2024.

Zhou et al., Systemic delivery of full-length dystrophin in Duchenne muscular dystrophy mice. Nat Commun. Jul. 21, 2024;15(1):6141. doi: 10.1038/s41467-024-50569-6.

* cited by examiner miR-17-5p CAAAGUGCUUACACAGUGCCAGGUAGU SEQ ID NO: 1 miR-20a-5p CAAAGUGCUUAUAGUGCAGGUAG SEQ ID NO: 2 miR-20b-5p CAAAGUGCUCAUAGUGCAGGUA SEQ ID NO: 13 miR-106a-5p CAAAGUGCUAACACAGUGCCAGGUA SEQ ID NO: 17 miR-106b-5p UAAAGUGCUGACAGUGCAGAU SEQ ID NO: 15 miR-93-5p CAAAGUGCUGUUCGUGCCAGGUAG SEQ ID NO: 18 ssAAV2-CBAp-
miRNA 17-92 scAAV2-CBAp-
miRNA 17-92

CLUSTAL Omega (1.2.4) multiple sequence alignment

| | |
|---|---|
| mouse | CAAAGTGCTTACAGTGCAGGTAGTGATGGTGCATCTACTGCAGTGAGGGCACTTGTAGC 60 |
| Human | caaagtgcttacacagtgcagtagtgatatgtgcatctactgcagtgaaggcacttgtagc 60 |
| | ** ********** ****** *** ***** *********************** ***** |

| | |
|---|---|
| mouse | ATTATGCTGACAGCTGCCTCGGTGGGAGCCACAGTGGGCGGCTGCCTCGGGGCGGCACTGGC 120 |
| Human | attatggtgacagctgcctcgggaagccaa------------------------------- 90 |
| | ****** ****************** ** ***** * |

| | |
|---|---|
| mouse | TGCGTCCAGTCGTCGGTCAGTCGGTCGGGGGGAGGGGCCTGCTGGTGCGTGCGGTGCTTTTTG 180 |
| Human | ------------gttgggcttaaagtgcaggtagtgcaggtggtgagtgctttttg 135 |
| | ** * ** * ** ** ********* |

| | |
|---|---|
| mouse | TTCTAAGGTGCATCTAGTGCAGATAGTGAAGTGAAGTAGAACTAGAACTCTACTGCCCTAAGTGCTC 240 |
| Human | ttctaaggtgcatctagtgcagatagtgcagatagtagtgaagtagcatctactgccctaagtgctc 195 |
| | ******************************** * ** ** *** *** ************* |

| | |
|---|---|
| mouse | CTTCTGCATAAGAAGTTATGTCCTCATCCAATCCAAGTC---AAGCAAGCATGTAGGGG 297 |
| Human | cttctggcataagaagttatgtatttcatccaataaattcaagccaagcaagtatatag-gt 254 |
| | ******* ************* *** ******** |

| | |
|---|---|
| mouse | TCTCTCCATAGTTGTGTGTTTGCAGCCCCTCCTTGTTAGTTTTGCATAGTTGCACTACAAGAAGA 357 |
| Human | gcttcaatagtttttgtttgcagtcctcctgtttagtttttgcatagtagttgcactacactacaagaaga 314 |
| | * ** ********* ** ** ** *** ** *** *** *** * **** ************ |

| | |
|---|---|
| mouse | ATGTAGTTGTGCAAATCTATGCAAAACTGATGGTGGGCCTGCTATTACTCAAGTGTTGT 417 (SEQ ID NO: 23) |
| Human | atgtagttgttgcaaaatctatgcaaaactgatggtggcctgctattccttcaaatgaatg 374 (SEQ ID NO: 24) |
| | ************ ********************** ** *** *** ** |

FIG. 7A

Underline: miR 17

Italic: miR 18a

Bold: miR 19a

Underline and Italic: miR 20a

Bold and Italic: miR 19b

Bold and underline: miR 92a

FIG. 7B

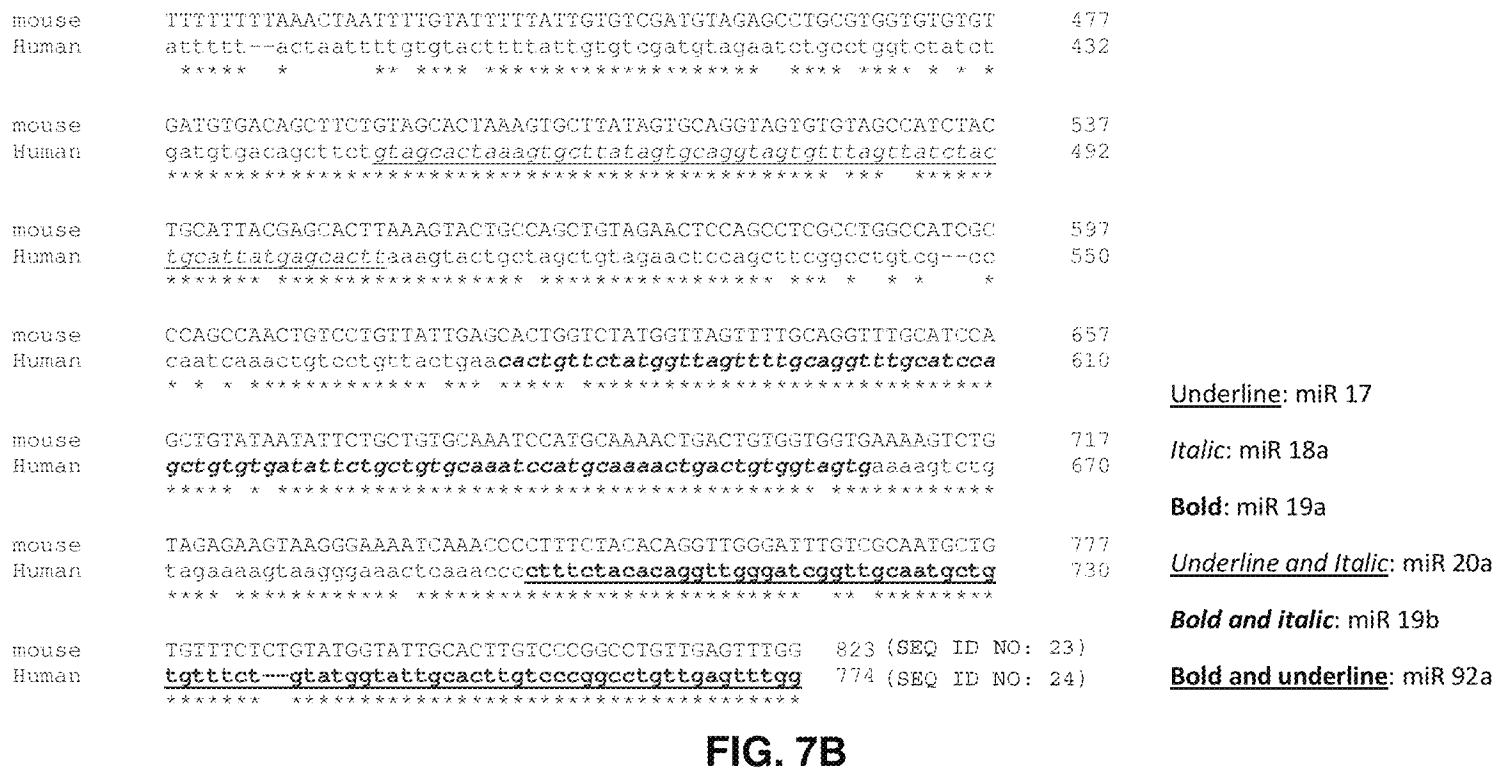

Underline: miR 17

*Italic*: miR 18a

Bold: miR 19a

<u>*Underline and Italic*</u>: miR 20a

*Bold and italic*: miR 19b

<u>Bold and underline</u>: miR 92a

SEQUENCE LISTING

```
<160> NUMBER OF SEQ ID NOS: 24

<210> SEQ ID NO 1
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 1
caaagugcuu acagugcagg uagu                                          24

<210> SEQ ID NO 2
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 2
uaaagugcuu auagugcagg uag                                           23

<210> SEQ ID NO 3
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 3
uaaggugcau cuagugcaga ua                                            22

<210> SEQ ID NO 4
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 4
ugugcaaauc uaugcaaaac uga                                           23

<210> SEQ ID NO 5
<211> LENGTH: 23
```

```
<212> TYPE: RNA
<213> ORGANISM: Artificial Sequence
<220> FEATURE:
<223> OTHER INFORMATION: Synthetic Polynucleotide

<400> SEQUENCE: 5
ugugcaaauc caugcaaaac uga                                        23

<210> SEQ ID NO 6
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 6
uauugcacuu gucccggccu g                                          21

<210> SEQ ID NO 7
<211> LENGTH: 6
<212> TYPE: RNA
<213> ORGANISM: Artificial Sequence
<220> FEATURE:
<223> OTHER INFORMATION: Synthetic Polynucleotide

<400> SEQUENCE: 7 aaagug                                                          6

<210> SEQ ID NO 8
<211> LENGTH: 145
<212> TYPE: DNA
<213> ORGANISM: adeno-associated virus 2

<400> SEQUENCE: 8
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcct                                     145

<210> SEQ ID NO 9
<211> LENGTH: 146
<212> TYPE: DNA
<213> ORGANISM: adeno-associated virus 3

<400> SEQUENCE: 9
ttggccactc cctctatgcg cactcgctcg ctcggtgggg cctggcgacc aaaggtcgcc   60
agacggacgt gctttgcacg tccggcccca ccgagcgagc gagtgcgcat agagggagtg  120
gccaactcca tcactagagg tatggc                                    146

<210> SEQ ID NO 10
<211> LENGTH: 142
<212> TYPE: DNA
<213> ORGANISM: Unknown
<220> FEATURE:
<223> OTHER INFORMATION: AAV6

<400> SEQUENCE: 10
ttgcccactc cctctatgcg cgctcgctcg ctcggtgggg cctgcggacc aaaggtccgc   60
agacggcaga gctctgctct gccggcccca ccgagcgagc gagcgcgcat agagggagtg  120
ggcaactcca tcactagggg ta                                        142

<210> SEQ ID NO 11
```

```
<211> LENGTH: 167
<212> TYPE: DNA
<213> ORGANISM: Unknown
<220> FEATURE:
<223> OTHER INFORMATION: AAV5

<400> SEQUENCE: 11
ctctcccccc tgtcgcgttc gctcgctcgc tggctcgttt gggggggtgg cagctcaaag        60
agctgccaga cgacggccct ctggccgtcg ccccccaaa cgagccagcg agcgagcgaa        120
cgcgacaggg gggagagtgc cacactctca agcaaggggg ttttgta                     167

<210> SEQ ID NO 12
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
```

```
        290              295              300

Trp Gly Phe Arg Pro Lys Arg Leu Asn Phe Lys Leu Phe Asn Ile Gln
305              310              315              320

Val Lys Glu Val Thr Thr Asn Asp Gly Val Thr Thr Ile Ala Asn Asn
                 325              330              335

Leu Thr Ser Thr Val Gln Val Phe Ser Asp Ser Glu Tyr Gln Leu Pro
                 340              345              350

Tyr Val Leu Gly Ser Ala His Gln Gly Cys Leu Pro Pro Phe Pro Ala
                 355              360              365

Asp Val Phe Met Ile Pro Gln Tyr Gly Tyr Leu Thr Leu Asn Asn Gly
                 370              375              380

Ser Gln Ala Val Gly Arg Ser Ser Phe Tyr Cys Leu Glu Tyr Phe Pro
385              390              395              400

Ser Gln Met Leu Arg Thr Gly Asn Asn Phe Thr Phe Ser Tyr Thr Phe
                 405              410              415

Glu Asp Val Pro Phe His Ser Ser Tyr Ala His Ser Gln Ser Leu Asp
                 420              425              430

Arg Leu Met Asn Pro Leu Ile Asp Gln Tyr Leu Tyr Phe Leu Asn Arg
                 435              440              445

Thr Gln Asn Gln Ser Gly Ser Ala Gln Asn Lys Asp Leu Leu Phe Ser
                 450              455              460

Arg Gly Ser Pro Ala Gly Met Ser Val Gln Pro Lys Asn Trp Leu Pro
465              470              475              480

Gly Pro Cys Tyr Arg Gln Gln Arg Val Ser Lys Thr Lys Thr Asp Asn
                 485              490              495

Asn Asn Ser Asn Phe Thr Trp Thr Gly Ala Ser Lys Tyr Asn Leu Asn
                 500              505              510

Gly Arg Glu Ser Ile Ile Asn Pro Gly Thr Ala Met Ala Ser His Lys
                 515              520              525

Asp Asp Lys Asp Lys Phe Phe Pro Met Ser Gly Val Met Ile Phe Gly
                 530              535              540

Lys Glu Ser Ala Gly Ala Ser Asn Thr Ala Leu Asp Asn Val Met Ile
545              550              555              560

Thr Asp Glu Glu Glu Ile Lys Ala Thr Asn Pro Val Ala Thr Glu Arg
                 565              570              575

Phe Gly Thr Val Ala Val Asn Leu Gln Ser Ser Ser Thr Asp Pro Ala
                 580              585              590

Thr Gly Asp Val His Val Met Gly Ala Leu Pro Gly Met Val Trp Gln
                 595              600              605

Asp Arg Asp Val Tyr Leu Gln Gly Pro Ile Trp Ala Lys Ile Pro His
                 610              615              620

Thr Asp Gly His Phe His Pro Ser Pro Leu Met Gly Gly Phe Gly Leu
625              630              635              640

Lys His Pro Pro Pro Gln Ile Leu Ile Lys Asn Thr Pro Val Pro Ala
                 645              650              655

Asn Pro Pro Ala Glu Phe Ser Ala Thr Lys Phe Ala Ser Phe Ile Thr
                 660              665              670

Gln Tyr Ser Thr Gly Gln Val Ser Val Glu Ile Glu Trp Glu Leu Gln
                 675              680              685

Lys Glu Asn Ser Lys Arg Trp Asn Pro Glu Val Gln Tyr Thr Ser Asn
                 690              695              700

Tyr Ala Lys Ser Ala Asn Val Asp Phe Thr Val Asp Asn Asn Gly Leu
705              710              715              720
```

```
Tyr Thr Glu Pro Arg Pro Ile Gly Thr Arg Tyr Leu Thr Arg Pro Leu
            725                 730                 735
```

```
<210> SEQ ID NO 13
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 13
uaaagugcug acagugcaga u                                                    21

<210> SEQ ID NO 14
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 14
caaagugcug uucgugcagg uag                                                  23

<210> SEQ ID NO 15
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 15
caaagugcuc auagugcagg uag                                                  23

<210> SEQ ID NO 16
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 16
caaagugcua acagugcagg ua                                                   22

<210> SEQ ID NO 17
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 17
aaaagugcuu acagugcagg uag                                                  23

<210> SEQ ID NO 18
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 18
caaagugcuc uucgugcagg uag                                                  23

<210> SEQ ID NO 19
<211> LENGTH: 23
```

```
<212> TYPE: RNA
<213> ORGANISM: Artificial Sequence
<220> FEATURE:
<223> OTHER INFORMATION: Synthetic Polynucleotide

<400> SEQUENCE: 19
caaagugcuu acagugcagg uag                                              23

<210> SEQ ID NO 20
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 20
caaagugcuc auagugcagg uag                                              23

<210> SEQ ID NO 21
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 21
aaaagugcuu acagugcagg uag                                              23

<210> SEQ ID NO 22
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 22
caaagugcuc uucgugcagg uag                                              23

<210> SEQ ID NO 23
<211> LENGTH: 823
<212> TYPE: DNA
<213> ORGANISM: Mus musculus

<400> SEQUENCE: 23
caaagtgctt acagtgcagg tagtgatgtg tgcatctact gcagtgaggg cacttgtagc      60
attatgctga cagctgcctc ggtgggagcc acagtgggcg ctgcctcggg cggcactggc     120
tgcgtccagt cgtcggtcag tcggtcgcgg ggagggcctg ctggtgctgc gtgctttttg     180
ttctaaggtg catctagtgc agatagtgaa gtagactagc atctactgcc ctaagtgctc     240
cttctggcat aagaagttat gtcctcatcc aatccaagtc aagcaagcat gtaggggtct     300
ctccatagtt gtgtttgcag ccctctgtta gttttgcata gttgcactac aagaagaatg     360
tagttgtgca aatctatgca aaactgatgg tggcctgcta tttacttcaa gtgttgtttt     420
tttttaaact aattttgtat ttttattgtg tcgatgtaga gcctgcgtgg tgtgtgtgat     480
gtgacagctt ctgtagcact aaagtgctta tagtgcaggt agtgtgtagc catctactga     540
attacgagca cttaaagtac tgccagctgt agaactccag cctcgcctgg ccatcgccca     600
gccaactgtc ctgttattga gcactggtct atggttagtt ttgcaggttt gcatccagct     660
gtataatatt ctgctgtgca aatccatgca aaactgactg tggtggtgaa aagtctgtag     720
agaagtaagg gaaaatcaaa cccctttcta cacaggttgg gatttgtcgc aatgctgtgt     780
```

-continued

```
ttctctgtat ggtattgcac ttgtcccggc ctgttgagtt tgg                    823

<210> SEQ ID NO 24
<211> LENGTH: 774
<212> TYPE: DNA
<213> ORGANISM: Homo sapiens

<400> SEQUENCE: 24
caaagtgctt acagtgcagg tagtgatatg tgcatctact gcagtgaagg cacttgtagc      60
attatggtga cagctgcctc gggaagccaa gttgggcttt aaagtgcagg gcctgctgat     120
gttgagtgct ttttgttcta aggtgcatct agtgcagata gtgaagtaga ttagcatcta     180
ctgccctaag tgctccttct ggcataagaa gttatgtatt catccaataa ttcaagccaa     240
gcaagtatat aggtgtttta atagtttttg tttgcagtcc tctgttagtt ttgcatagtt     300
gcactacaag aagaatgtag ttgtgcaaat ctatgcaaaa ctgatggtgg cctgctattt     360
ccttcaaatg aatgattttt actaattttg tgtactttta ttgtgtcgat gtagaatctg     420
cctggtctat ctgatgtgac agcttctgta gcactaaagt gcttatagtg caggtagtgt     480
ttagttatct actgcattat gagcacttaa agtactgcta gctgtagaac tccagcttcg     540
gcctgtcgcc caatcaaact gtcctgttac tgaacactgt tctatggtta gttttgcagg     600
tttgcatcca gctgtgtgat attctgctgt gcaaatccat gcaaaactga ctgtggtagt     660
gaaaagtctg tagaaaagta agggaaactc aaaccccttt ctacacaggt tgggatcggt     720
tgcaatgctg tgtttctgta tggtattgca cttgtcccgg cctgttgagt ttgg           774
```

ENHANCED TRANSDUCTION OF AAV VECTORS ENCODING MICRORNAS

RELATED APPLICATIONS

This application is a national stage filing under 35 U.S.C. 371 of International Patent Application Serial No. PCT/US2020/027927, filed Apr. 13, 2020, which claims benefit of U.S. Provisional Application No. 62/833,662, filed Apr. 13, 2019 The entire contents of these applications are incorporated herein by reference in their entireties.

SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Mar. 31, 2022, is named U119670038US01-SUBSEQ-EPG and is 13,611 bytes in size.

BACKGROUND

Adeno-associated virus (AAV) particles are promising as effective gene delivery tools for long term transduction of a desired gene product in a broad range of tissues for numerous diseases and medical conditions. Despite the generation of second and third generation AAV capsids, these vectors exhibit some shortcomings in efficiency of transduction of target cells. Thus, there exists a need in the art for engineered AAV vectors with enhanced transduction efficiencies.

It has been reported that the infection of human cells by AAV2 vectors leads to the activation of the glucocorticoid receptor (GR) signaling pathway, and leads to the binding of GR to the D-sequence within the inverted terminal repeat (ITR) of the AAV2 genome, which shares partial homology to the consensus half-site of the glucocorticoid receptor response element (GRE). See Lu et al., Involvement of the Glucocorticoid Receptor Signaling in AAV2 Vector-Mediated Transgene Expression, *Mol. Ther.,* 18(S1): S276 (2010).

SUMMARY OF THE INVENTION

The present disclosure is based, at least in part, on the observation that co-infection of a viral vector-expressed transgene of interest with an AAV vector-expressed microRNA (miRNA) sequence that targets the glucocorticoid receptor (GR) pathway increases the transduction efficiency of the transgene. This transduction enhancement is observed both with the use of single-stranded AAV ("ssAAV") and self-complementary AAV ("scAAV") vectors.

Recently, it was reported that substitution of the D-sequence found within the inverted terminal repeat (ITR) regions of the AAV genome with authentic glucocorticoid response element (GRE) sequences further increases AAV2 vector-mediated transgene expression. See Ling et al., The Role of Glucocorticoid Receptor Signaling in Adeno-Associated Virus 2 Infection, *Mol. Ther.,* 24, 51: S6 (2016). It has become clear that the GR pathway, and potentially GRE activation specifically, plays a role in AAV2 vector-mediated transgene expression. It was also reported that microRNA-17-92 ("microRNA 17-92" or "miR17-92") mediates activation of the GR pathway. See Jin et al., miR-17-92 Cluster Regulates Adult Hippocampal Neurogenesis, Anxiety, and Depression, *Cell Rep.,* 16: 1653-1663 (2016), herein incorporated by reference. This group determined that the expression levels of multiple genes, known to be involved in cell proliferation and differentiation, were altered in the hippocampus of miR-17-92 KO mice. Particularly, the alterations in the level of multiple genes that are implicated in glucocorticoid-mediated pathways were observed in the hippocampus of miR-17-92 KO mice.

In particular embodiments of the disclosure, the miRNA sequence of the disclosed rAAV nucleic acids that targets the GR pathway is the polycistronic miR17-92 cluster, which comprises six miRNA sequences operably controlled by a single promoter. The miR17-92 cluster consists of miR-17 (sometimes written as miR-17-5p), miR-20a, miR-18a, miR-19a, miR-19b-1 and miR-92a-1. In other embodiments, the miRNA sequence comprises one, two or more members of the miR-17 family. The miR-17 family consists of miR-17, miR-20a, miR-20b, miR-106a, miR-106b, and miR-93.

In other aspects, the present disclosure provides compositions comprising recombinant AAV particles comprising nucleic acids comprising a transgene of interest, or heterologous nucleic acid, and the miR17-92 cluster. The present disclosure also provides methods of administering these compositions. In some embodiments, the methods comprise delivery of two or more rAAV particles, a first particle comprising a nucleic acid comprising the transgene and a second particle comprising a nucleic acid encoding the miR17-92 cluster, i.e., delivery in trans. In other embodiments of the disclosed methods, the transgene and miR17-92 cluster are encoded onto a single nucleic acid incorporated into an AAV genome and administered using a single rAAV particle, i.e., delivery in cis.

In some embodiments, the nucleic acid is single-stranded. In other embodiments, the nucleic acid is double-stranded. In particular embodiments of double-stranded nucleic acids, the nucleic acid is self-complementary.

In some aspects, the present disclosure provides rAAV particles comprising a nucleic acid segment encoding one, two or more miRNA sequences that may regulate the GR pathway. In some embodiments, the rAAV particle is selected from serotypes AAV2, AAV3, AAV6, AAV8, and AAV9. In some embodiments, the rAAV particle is an rAAV2 particle, optionally further comprising a non-tyrosine residue at each of Y444, Y500 and Y730 of a wild-type AAV2 capsid protein. In some embodiments, the rAAV particle is an rAAV8 particle.

In certain aspects, the present disclosure provides compositions comprising a first nucleic acid (e.g., a single-stranded or self-complementary rAAV genome) comprising a heterologous nucleic acid encoding a miRNA that inhibits GR activity, and a second nucleic acid (e.g., a single-stranded AAV genome) comprising a heterologous nucleic acid encoding a transgene of interest. In particular embodiments, the transgene of interest comprises Factor IX. In some embodiments, the transgene of interest comprises wild-type Factor IX or Factor IX, Padua mutant. In other embodiments, the transgene of interest comprises Factor XIII. In some embodiments, the first nucleic acid and second nucleic acid are comprised (or packaged) within two (or more) rAAV particles.

In some aspects, the present disclosure provides compositions comprising a single nucleic acid (e.g., a single-stranded or self-complementary rAAV genome) that comprises a heterologous nucleic acid encoding a miRNA that inhibits GR activity, and a heterologous nucleic acid encoding a transgene of interest. In some embodiments, the single nucleic acid is comprised within a single rAAV particle.

In certain embodiments, the miRNA comprises a cluster of polycistronic miRNAs. In certain embodiments, the miRNA comprises a subset of a cluster of polycistronic miRNAs. In certain embodiments, the miRNA is an miR17-92 cluster. In some embodiments, the miRNA comprises a subset of a family of miRNAs related by a common seed sequence. In particular embodiments, the miRNA is an miR-17 family.

In some embodiments, the first nucleic acid (encoding an miRNA) is encapsidated within a first rAAV particle and the second nucleic acid (encoding a transgene of interest) is encapsidated within a second rAAV particle. In certain embodiments, the ratio of the first rAAV particle to the second rAAV particle is about 10:1. In certain embodiments, the ratio of the first rAAV particle to the second rAAV particle is about 15:1, about 13:1, about 12:1, about 11:1, about 21:2, about 19:2, about 9:1, about 8:1, about 7:1, about 6:1 or about 5:1.

In particular embodiments, at least one of the first or second rAAV nucleic acids is self-complementary. In some embodiments, the first and second rAAV particles are of the same serotype selected from AAV2, AAV3, AAV6, and AAV8. In particular embodiments, the first and second rAAV particles are AAV2 particles. In particular embodiments, the first and second rAAV particles are self-complementary (scrAAV2) rAAV2 particles. In other embodiments, the first and second rAAV particles are AAV8 particles. In some embodiments, the first and second rAAV particles are scrAAV8 particles.

In other embodiments, the disclosed nucleic encodes both a gene of interest and an miRNA sequence, e.g., an miRNA cluster or a subset of miRNAs from the cluster. In particular embodiments, the disclosed nucleic acid is contained within an rAAV particle (e.g., the central nucleic acid segment that is flanked by the two ITRs) and encodes both a gene of interest and an miRNA sequence.

In other aspects, the present disclosure provides methods of transducing a cell comprising administering an effective amount of the disclosed compositions. In some embodiments, the cell to be transduced is a mammalian cell. In particular embodiments, the cell is a human cell.

In some embodiments, the disclosure provides methods of contacting a cell with a microRNA that knocks down GR activity, e.g., methods of increasing rAAV transduction efficiency comprising contacting a cell with a microRNA that downregulates GR activity. In some embodiments, the microRNA is encoded in an rAAV vector. In particular embodiments, methods of increasing transduction efficiency comprising contacting a cell with an rAAV2-miR17-92 vector are provided. In certain embodiments, methods of increasing transduction efficiency comprising contacting a cell with an rAAV8-miR17-92 vector are provided. In certain embodiments, methods of increasing transduction efficiency comprising contacting a cell with an scrAAV8-miR17-92 vector are provided.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

In FIG. 3A, mCherry expression (lighter-colored regions) was visualized by fluorescence microscopy in mock-infected or scAAV2-mCherry vector-transduced HeLa cells either in the absence or the presence of various indicated amounts of miRNA 17-92 expression plasmid. FIG. 3B represents a quantitation of the data from FIG. 3A.

In FIG. 4A, EGFP expression (light-colored regions) was visualized by fluorescence microscopy in mock-infected or scAAV2-EGFP vector-transduced HeLa cells either in the absence or the presence of various indicated amounts of miRNA 17-92 expression plasmid. FIG. 4B represents a quantitation of the data from FIG. 4A.

In FIG. 5A, EGFP expression was visualized by fluorescence microscopy in mock-infected or ssAAV2-EGFP or scAAV2-EGFP vector-transduced HeLa cells either in the absence or the presence of co-transduction with scAAV2-miRNA 17-92 vectors. FIG. 5B represents a quantitation of the data from FIG. 5A.

In FIG. 6A, EGFP expression was visualized by fluorescence microscopy in mock-infected or ssAAV2-EGFP vector-transduced HeLa cells either in the absence or the presence of miRNA 17-92. FIG. 6B represents a quantitation of the data from FIG. 6A.

FIGS. 7A-7B depict an alignment of the regions of human and mouse chromosome 13q31.3 that encode the polycistronic miR17-92 cluster sequence.

DETAILED DESCRIPTION

Aspects of this disclosure relate to nucleic acids that have been engineered to include microRNAs (miRNAs) that regulate the GR pathway and/or enhance transduction efficiencies of transgenes expressed in single-stranded AAV genomes.

Accordingly, disclosed herein are compositions comprising a first nucleic acid segment encoding one or more miRNA sequences and a second nucleic acid segment encoding a transgene of interest. In certain embodiments, the nucleic acid segment is a plasmid. In other embodiments, the nucleic acid segment is encapsidated in an rAAV particle. Further disclosed are methods comprising administering a first nucleic acid segment encoding one or more miRNA sequences and a second nucleic acid segment encoding a transgene of interest to a target cell.

miRNAs are short, non-coding RNA sequences, typically 19-22 nucleotides in length, that form stem-loop hairpin structures that mediate post-transcriptional downregulation of messenger RNA (mRNA) protein expression. This downregulation occurs by sequence-specific recognition of seed sequences predominantly in the 3' UTR of target mRNAs. Approximately 60% of the mammalian transcriptome is subject to regulation by miRNAs. See Clayton et al., *J. Biol Chem.* 2018; 293(6): 1865-1874, herein incorporated by reference.

Mechanistically, miRNAs exert their effects based on complementarity with their target messenger RNA sequences. Watson-Crick base-pairing between a seed sequence, a stretch of 6 nucleotides (2 through 8) at the 5' end of a mature miRNA, and a complementary sequence on target mRNA results in the repression of that mRNA. The miRNA functions as part of an RNA-induced silencing complex (RISC), in which the Argonaute family of proteins plays a major role. The mature miRNA is loaded onto Argonaute, and the passenger strand is removed and degraded, resulting in the final active complex containing a one-stranded miRNA species complementary to a portion of the target gene 3' UTR. miRNAs that harbor the same seed are classified into a single family, and accordingly, miRNAs belonging to the same family have redundant biological functions.

Figures 1A, 1B:
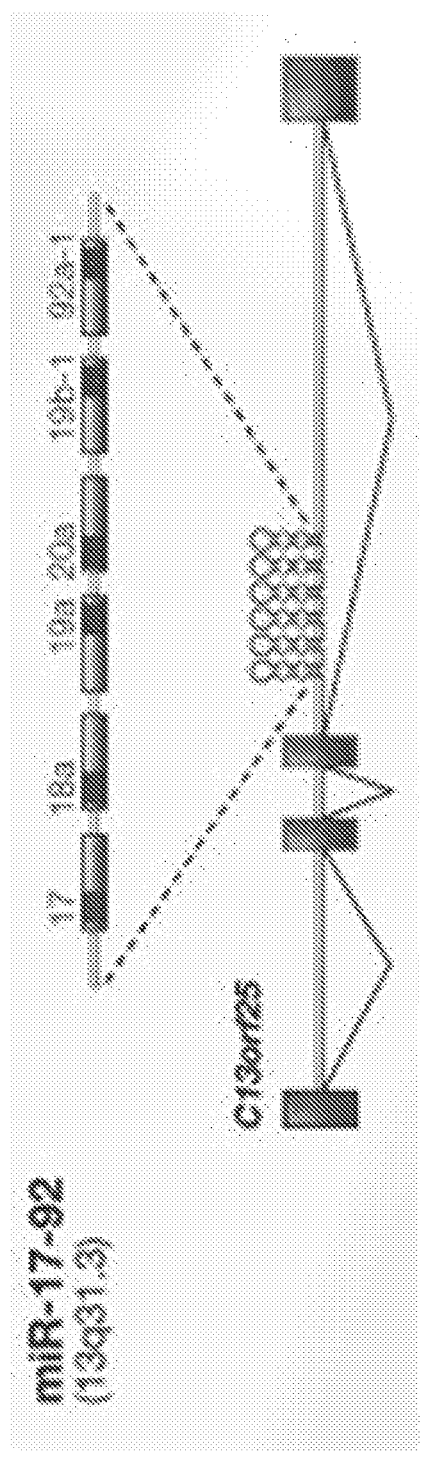
FIGS. 1A-1B show the structure of a miRNA 17-92 cluster (FIG. 1A) and associated nucleotide sequences (FIG. 1B).

The miR17-92 gene MIR17HG, which is located at chromosome 13q31.3, is a polycistronic sequence that encodes six microRNAs that belong collectively to the miR-17, miR-18, miR-19 and miR-92 families (FIG. 1A). The transcript derived from this gene comprises six tandem stem-loop hairpin structure which results in six mature miRNAs: miR-17-5p, miR-18a, miR-19a, miR-20a, miR-19b-1 and miR-92a-1. See Gruszka & Zakrewska, *Int. J. Mol. Sci.* 19, 879 (2018), herein incorporated by reference. The miR17-92 cluster is conserved among vertebrates. The human genome contains two paralogues of the miR17-92 cluster: the miR-106b/25 and the miR-106a/363 cluster. The miR-106b/25 cluster comprises three miRNAs: miR-106b, miR-93 and miR-25. Whereas the miR-106a/363 cluster comprises six miRNAs: miR-106a, miR-18b, miR-20b, miR-19b-2, miR-92a-2 and miR-363. All three such clusters contain the same six-nucleotide seed sequence, AAAGUG (SEQ ID NO: 7). See Mogilyansky & Rigoutsos, *Cell Death and Differentiation,* 2013; 20: 1603-1614, herein incorporated by reference.

It has been reported that miR17-92 regulates genes in the glucocorticoid pathway, especially serum- and glucocorticoid-inducible protein kinase-1 (Sgk1), a downstream effector of GR. miR17-92 knockout mice show anxiety- and depression-like behaviors, whereas miR-17-92-overexpressing mice exhibit anxiolytic and antidepression-like behaviors. See Jin et al., miR-17-92 Cluster Regulates Adult Hippocampal Neurogenesis, Anxiety, and Depression, *Cell Rep.,* 16: 1653-1663 (2016), herein incorporated by reference. It has also been reported that glucocorticoid agents upregulate endogenous expression of miRNAs in multiple cell types. See Clayton et al., *J. Biol Chem.* 2018; 293(6). An alignment of the regions of human chromosome 13q31.3 and mouse (Mus musculus) chromosome 13q31.3 that encode the miR17-92 cluster sequences is illustrated in in FIGS. 7A-7B.

Figure 2:
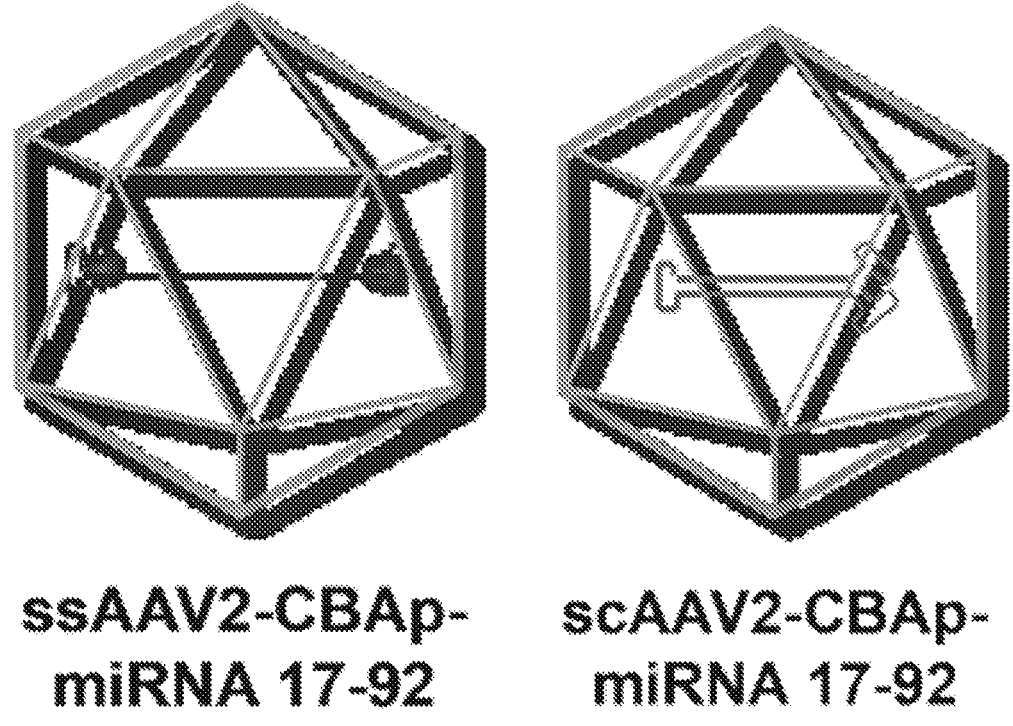
FIG. 2 is a schematic showing the structures of ssAAV2 and scAAV2-miRNA 17-92 vectors. Abbreviation: CBAp, Chicken β-actin promoter.

In certain aspects, the present disclosure provides recombinant AAV (rAAV) particles comprising single-stranded rAAV nucleic acids containing a nucleic acid segment encoding one, two or more miRNA sequences that may regulate the GR pathway. These single-stranded rAAV nucleic acids may be self-complementary (see FIG. 2). These nucleic acids may alter the expression of Sgk1, e.g., by regulating Sgk1 mRNA.

As used herein, the term "miR17-92 cluster" refers to the six mature miRNAs generated from the single precursor transcript expressed by MIR17HG, i.e., miR-17 (sometimes written as miR-17-5p), miR-20a, miR-18a, miR-19a, miR-19b-1 and miR-92a-1. The sequences of these miRNAs are provided below, in order of which they are positioned endogenously:

```
miR-17(-5p):
                            (SEQ ID NO: 1)
CAAAGUGCUUACAGUGCAGGUAGU miR-20a:
                            (SEQ ID NO: 2)
UAAAGUGCUUAUAGUGCAGGUAG miR-18a:
                            (SEQ ID NO: 3)
UAAGGUGCAUCUAGUGCAGAUA miR-19a:
                            (SEQ ID NO: 4)
UGUGCAAAUCUAUGCAAAACUGA miR-19b-1:
                            (SEQ ID NO: 5)
UGUGCAAAUCCAUGCAAAACUGA miR-92a-1:
                            (SEQ ID NO: 6)
UAUUGCACUUGUCCCGGCCUG
```

The miRNA-encoding sequence incorporated into the rAAV nucleic acids disclosed herein may comprise a DNA sequence encoding the full miRNA 17-92 cluster, as this sequence occurs endogenously in MIR17HG. In certain embodiments, the miRNA sequence incorporated into the rAAV nucleic acids (e.g., single-stranded or self-complementary rAAV nucleic acids) disclosed herein may comprise at least one, two, three, four, five or six sequences selected from SEQ ID NOs: 1-6, above.

In some embodiments, an rAAV nucleic acid comprises a nucleic acid sequence encoding a full miRNA 17-92 cluster, one or more miRNAs from the cluster, one or more of miR-17, miR-20a, miR-18a, miR-19a, miR-19b-1, miR-92a-1, or one or more precursors of any one or more thereof, such as premiRNA precursors of SEQ ID NOs: 1-6. One or more (e.g., all) of the miRNA or premiRNA sequences may be human, mouse, or other mammalian (e.g., primate) sequence(s).

In some embodiments, the heterologous nucleic acid encodes a first miRNA sequence comprising SEQ ID NO: 1 and a second miRNA sequence comprising SEQ ID NO: 2. In other embodiments, the nucleotide sequences of one or more of the one or more miRNA sequences differ by one or two nucleotides relative to a sequence selected from SEQ ID NOs: 1-6. These differences may comprise nucleotides that have been inserted, deleted, or substituted relative to the sequence of SEQ ID NO: 1, 2, 3, 4, 5 or 6. These differences may otherwise comprise truncations at the 5' or 3' end relative to SEQ ID NO: 1, 2, 3, 4, 5 or 6. In certain embodiments, the nucleotide sequences of one or more of the one or more miRNA sequences differ by three, four or five nucleotides relative to a sequence selected from SEQ ID NOs: 1-6. In other embodiments, the nucleotide sequences of each of the one or more miRNA sequences differ by one, two, three, four or five nucleotides relative to a sequence selected from SEQ ID NOs: 1-6.

In other embodiments, the nucleotide sequences of one or more of the one or more miRNA sequences differ by one, two, three, four or five nucleotides relative to a sequence selected from SEQ ID NOs: 13-16. In other embodiments, the nucleotide sequences of each of the one or more miRNA sequences differ by one, two, three, four or five nucleotides relative to a sequence selected from SEQ ID NOs: 13-16. These differences may comprise nucleotides that have been inserted, deleted, or substituted relative to the sequence of SEQ ID NOs: 13-16. These differences may otherwise comprise truncations at the 5' or 3' end relative to SEQ ID NOs: 13-16.

In some embodiments, the miRNA sequence incorporated into the rAAV nucleic acids disclosed herein may comprise at least one, two, three, four, five or six sequences selected from miR-17, miR-20a, miR-20b, miR-106a, miR-106b, and miR-93. These sequences comprise the miR-17 family and are related by a common targeted seed sequence. Two such sequences, miR-17 and miR-20a, are also members of the miR17-92 cluster.

Accordingly, in certain embodiments, the present disclosure provides rAAV particles comprising a rAAV nucleic acid (e.g., single-stranded or self-complementary) comprising a heterologous nucleic acid encoding sequences comprising one or more miRNA sequence selected from SEQ ID NOs: 1-2 and 13-16, for example any two, three, four, five or all six of these miRNAs. In particular embodiments, the heterologous nucleic acid comprises a nucleic acid segment encoding sequences comprising at least two miRNA sequences selected from SEQ ID NOs: 1-6 or SEQ ID NOs: 13-16. In particular embodiments, the heterologous nucleic acid comprises a nucleic acid segment encoding miRNA sequences comprising each of SEQ ID NOs: 1-2 and SEQ ID NOs: 13-16.

```
miR-17:
                              (SEQ ID NO: 1)
CAAAGUGCUUACAGUGCAGGUAGU miR-20a:
                              (SEQ ID NO: 2)
UAAAGUGCUUAUAGUGCAGGUAG miR-20b:
                              (SEQ ID NO: 13)
CAAAGUGCUCAUAGUGCAGGUA miR-106a:
                              (SEQ ID NO: 14)
CAAAGUGCUGUUCGUGCAGGUAG miR-106b:
                              (SEQ ID NO: 15)
UAAAGUGCUGACAGUGCAGAU miR-93:
                              (SEQ ID NO: 16)
CAAAGUGCUAACAGUGCAGGUA
```

In some embodiments, an rAAV nucleic acid comprises a nucleic acid sequence encoding a full miRNA-17 family, one or more miRNAs from the family, one or more of miR-17, miR-20a, miR-20b, miR-106a, miR-106b, miR-93, or one or more precursors of any one or more thereof, such as premiRNA precursors of SEQ ID NOs: 1, 2, and 13-16. One or more (e.g., all) of the miRNA or premiRNA sequences may be human, mouse, or other mammalian (e.g., primate) sequence(s).

In some embodiments, the miRNA sequence incorporated into the rAAV nucleic acids disclosed herein may comprise at least one, two, three, four, five or six sequences selected from the miRNA family of sequences shown in FIG. 1B. In certain embodiments, the present disclosure provides rAAV particles comprising a rAAV nucleic acid (e.g., single-stranded or self-complementary) comprising a heterologous nucleic acid encoding one or more miRNA sequences selected from SEQ ID NOs: 1, 2, 13, 15, and 17-22, for example any one, two, three, four, five or all six of these miRNAs. In some embodiments, the heterologous nucleic acid comprises a nucleic acid segment encoding sequences comprising at least two miRNA sequences selected from SEQ ID NOs: 17-22. In some embodiments, the heterologous nucleic acid comprises a nucleic acid segment encoding miRNA sequences comprising each of SEQ ID NOs: 1, 2, 13, 15, 17, and 18. In some embodiments, the heterologous nucleic acid comprises a nucleic acid segment encoding miRNA sequences comprising each of SEQ ID NOs: 2, 19, 20, 21, 22, and 15. In some embodiments, an rAAV nucleic acid comprises one or more precursors, such as premiRNA precursors, of SEQ ID NOs: 1, 2, 13, 15, and 17-22. One or more (e.g., all) of these miRNA or premiRNA sequences may be human, mouse, or other mammalian (e.g., primate) sequence(s).

```
miR-17(-5p):
                              (SEQ ID NO: 19)
CAAAGUGCUUACAGUGCAGGUAG miR-20b:
                              (SEQ ID NO: 20)
CAAAGUGCUCAUAGUGCAGGUAG miR-106a:
                              (SEQ ID NO: 21)
AAAAGUGCUUACAGUGCAGGUAG miR-93:
                              (SEQ ID NO: 22)
CAAAGUGCUCUUCGUGCAGGUAG
```

In other embodiments, the nucleotide sequences of each of the one or more miRNA sequences differ by one, two, three, four or five nucleotides relative to a sequence selected from SEQ ID NOs: 19-22. These differences may comprise nucleotides that have been inserted, deleted, or substituted relative to the sequence of SEQ ID NOs: 19-22. These differences may otherwise comprise truncations at the 5' or 3' end relative to SEQ ID NOs: 19-22.

In some embodiments of the disclosed vectors, the complementary sequence of any one or more of the sequences described herein, e.g., SEQ ID NOs: 1-22, may be comprised or encoded within a heterologous nucleic acid. It should be appreciated that miRNAs from different species may be used to carry out the advantages of the disclosure (e.g., distinct sequences from distinct species set forth in this disclosure and the sequence listing filed herewith).

In certain embodiments, the rAAV particle is an AAV2 particle. In other embodiments, the rAAV particle is an AAV8 particle. In some embodiments, the AAV2 particle comprises a modified capsid protein comprising a non-tyrosine residue at a position that corresponds to a surface-exposed tyrosine residue in a wild-type AAV2 capsid protein, a non-threonine residue at a position that corresponds to a surface-exposed threonine residue in the wild-type AAV2 capsid protein, a non-lysine residue at a position that corresponds to a surface-exposed lysine residue in the wild-type AAV2 capsid protein, a non-serine residue at a position that corresponds to a surface-exposed serine residue in the wild-type AAV2 capsid protein, or a combination thereof. In some embodiments, the modified AAV2 capsid protein comprises a non-tyrosine residue at each of Y444, Y500 and Y730 of a wild-type AAV2 capsid protein.

The increase in transgene expression from the exemplary single-stranded AAV2 vectors disclosed herein may be about 2-fold when the miRNA 17-92 cluster is co-expressed in cis. Remarkably, the increase in transgene expression from ssAAV vectors may be about 2-fold when the miRNA 17-92 cluster is co-administered in trans.

The presently disclosed transgenes of interest may encode a therapeutic protein, such as Factor IX or Factor VIII. In other embodiments, the transgenes encode a reporter gene. In some embodiments, the therapeutic protein is selected from the group consisting of adrenergic agonists, anti-apoptosis factors, apoptosis inhibitors, cytokine receptors, cytokines, cytotoxins, erythropoietic agents, glutamic acid decarboxylases, glycoproteins, growth factors, growth factor receptors, hormones, hormone receptors, interferons, interleukins, interleukin receptors, kinases, kinase inhibitors, nerve growth factors, netrins, neuroactive peptides, neuroactive peptide receptors, neurogenic factors, neurogenic factor receptors, neuropilins, neurotrophic factors, neurotrophins, neurotrophin receptors, N-methyl-D-aspartate antagonists, plexins, proteases, protease inhibitors, protein decarboxylases, protein kinases, protein kinase inhibitors, proteolytic proteins, proteolytic protein inhibitors, semaphorins, semaphorin receptors, serotonin transport proteins, serotonin uptake inhibitors, serotonin receptors, serpins, serpin receptors, and tumor suppressors.

In some embodiments, the transgene of interest is about 2- to about 5-kb in length. In particular embodiments, the transgene of interest is about 4- to about 5-kb in length. Further aspects of this disclosure relate to compositions comprising a first rAAV nucleic acid (e.g., single-stranded or self-complementary) comprising a heterologous nucleic acid encoding a miRNA that inhibits GR activity, and a second single-stranded rAAV nucleic acid (e.g., single-stranded or self-complementary) comprising a heterologous nucleic acid encoding a transgene of interest. In certain embodiments, the miRNA is an miR17-92 cluster. In other embodiments, the miRNA is a subset of the miR17-92 cluster. In still other embodiments, the miRNA is a subset of the miR-17 family.

In some embodiments, the compositions further comprise a tyrphostin, or tyrosine kinase inhibitor. Tyrphostins are known to promote AAV second-strand DNA synthesis.

In certain embodiments, the disclosed compositions further comprise a pharmaceutically acceptable excipient.

Further aspects of this disclosure relate to methods of transducing a host cell comprising administering an effective amount of the disclosed compositions. In some embodiments, the disclosed methods comprise delivery of the miRNA-expressing nucleic acid and transgene-expressing nucleic acid in trans. In particular embodiments, the miRNA-expressing nucleic acid is administered prior to the administration of the transgene-expressing nucleic acid. In other embodiments, the miRNA-expressing nucleic acid is administered subsequent to the administration of the transgene-expressing nucleic acid. In still other embodiments, these components are co-administered at about the same time.

In other embodiments, the disclosed methods comprise delivery of these nucleic acids in cis.

In certain embodiments of the disclosed methods, the ratio of the first rAAV particle (comprising a first nucleic acid encoding the miRNA) to the second rAAV particle (comprising a second nucleic acid encoding the transgene) is about 10:1. In other embodiments, the ratio is about 13:1, 12:1, 21:2, 19:2, 9:1, 8:1, 7:1, 6:1 or 5:1. In particular embodiments, at least one of the first or second AAV nucleic acids is self-complementary.

Subsequent to the administration of the disclosed nucleic acid encoding an miR17-92, a target sequence in the GR pathway may be knocked down or downregulated. This downregulation may facilitate the enhanced transduction efficiencies observed following co-administration of these particles with transgene-expressing rAAV particles. For instance, transgene expression may be increased by a factor of 2. In some embodiments, transgene expression is increased by a factor of 3, 4, 5, 6, 7 or 8. In certain embodiments, transgene expression is increased by a factor of more than 10.

Any host cell is contemplated for use in a method described herein. In some embodiments, the host cell to be transduced is a mammalian cell. In particular embodiments, the cell is a human cell. In other embodiments, the host cell is a human cell, a non-human primate cell, a dog cell, a cat cell, a mouse cell, a rat cell, a guinea pig cell, or a hamster cell. In some embodiments, the host cell is a cell in situ in a host, such as a subject as described herein. In some embodiments, the host cell is ex vivo, e.g., in a culture of host cells.

In certain embodiments, the mammalian eye cell is selected from the group consisting of an ON retinal bipolar cell, an OFF retinal bipolar cell, a rod bipolar cell, and a cone bipolar cell. In some embodiments, the host cell is a stem cell, such as a hematopoietic stem cell (e.g., a human hematopoietic stem cell). In some embodiments, the host cell is a liver cell, muscle cell, brain cell, eye cell, pancreas cell, or kidney cell.

In some embodiments, the disclosed transduction methods further comprise administering a typhostin.

Pharmaceutical Compositions

As described herein, further provided herein are pharmaceutical compositions that comprise a modified rAAV vector as disclosed herein, and further comprise a pharmaceutical excipient, and may be formulated for administration to host cell ex vivo or in situ in an animal, and particularly a human. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions, diseases or disorders as described herein.

The term "excipient" refers to a diluent, adjuvant, carrier, or vehicle with which the rAAV particle or preparation, or nucleic acid segment is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

In certain embodiments, the present disclosure provides a method of reducing AAV immunity in a subject, wherein the method further comprises administering to the subject a composition comprising the disclosed rAAV particles and a pharmaceutically acceptable excipient, optionally wherein the subject has been previously administered a composition comprising rAAV particles. In particular embodiments, the subject is a human.

In some embodiments, the number of rAAV particles administered to a host cell may be on the order ranging from 500 to 5,000 vgs/cell. In particular embodiments, the disclosed methods comprise administration of rAAV particles in doses of about 500 vgs/cell, 1000 vgs/cell, 2000 vgs/cell, 3000 vgs/cell, 4000 vgs/cell, 5000 vgs/cell, 6000 vgs/cell or 7000 vgs/cell.

In some embodiments, the number of rAAV particles administered to a subject may be on the order ranging from $10^6$ to $10^{14}$ particles/mL or $10^3$ to $10^{13}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are be administered. In some embodiments, the number of rAAV particles administered to a subject may be on the order ranging from $10^6$ to $10^{14}$ vector genomes(vgs)/mL or $10^3$ to $10^{15}$ vgs/mL, or any values therebetween for either range, such as for example, about $10^6$, $10^7$, $10^8$, $10^9$, $10^{10}$, $10^{11}$, $10^{12}$, $10^{13}$, or $10^{14}$ vgs/mL. In certain embodiments, the disclosed methods comprise administration of rAAV particle compositions in doses of $3 \times 10^3$-$1 \times 10^4$ vgs/mL. In one embodiment, rAAV particles of higher than $10^{13}$ vgs/mL are be administered.

The rAAV particles can be administered as a single dose, or divided into two or more administrations as may be required to achieve therapy of the particular disease or disorder being treated. In some embodiments, 0.0001 mL to 10 mLs are delivered to a subject. In some embodiments, interferon-γ is co-administered with the rAAV particles. In some embodiments, interferon-γ is administered after administration of the rAAV particles.

In some embodiments, the disclosure provides formulations of compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particle or preparation and nucleic acid segments may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles or preparations and nucleic acid segments may thus be delivered along with various other agents as required in the particular instance. Such compositions may be purified from host cells or other biological sources, or alternatively may be chemically synthesized as described herein. As used herein, the term "vector" can refer to a nucleic acid segment (e.g., a plasmid or recombinant viral genome) or a viral vector (e.g., an rAAV particle comprising a recombinant genome).

Formulation of pharmaceutically-acceptable excipients is well-known to those of skill in the art, as is the development of suitable dosing and treatment regimens for using the particular compositions described herein in a variety of treatment regimens, including e.g., oral, parenteral, intravenous, intranasal, intra-articular, and intramuscular administration and formulation.

Typically, these formulations may contain at least about 0.1% of the therapeutic agent (e.g., rAAV particle or preparation and/or nucleic acid segment) or more, although the percentage of the active ingredient(s) may, of course, be varied and may conveniently be between about 1 or 2% and about 70% or 80% or more of the weight or volume of the total formulation. Naturally, the amount of therapeutic agent (s) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV particles or preparations and/or nucleic acid segments in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

The pharmaceutical forms of the compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The pharmaceutical compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles or preparations and/or nucleic acid segments, in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Ex vivo delivery of cells transduced with rAAV particles or preparations is also contemplated herein. Ex vivo gene delivery may be used to transplant rAAV-transduced host cells back into the host. A suitable ex vivo protocol may include several steps. For example, a segment of target tissue or an aliquot of target fluid may be harvested from the host and rAAV particles or preparations may be used to transduce a nucleic acid segment into the host cells in the tissue or fluid. These genetically modified cells may then be transplanted back into the host. Several approaches may be used for the reintroduction of cells into the host, including intravenous injection, intraperitoneal injection, or in situ injection into target tissue. Autologous and allogeneic cell transplantation may be used according to the invention.

The amount of rAAV particle or preparation or nucleic acid segment compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle or preparation or nucleic acid segment compositions, either over a relatively short, or a relatively prolonged period of time, as may be determined by the medical practitioner overseeing the administration of such compositions.

The composition may include rAAV particles or preparations or nucleic acid segments, either alone, or in combination with one or more additional active ingredients, which may be obtained from natural or recombinant sources or chemically synthesized. In some embodiments, rAAV particles or preparations are administered in combination, either in the same composition or administered as part of the same treatment regimen, with a proteasome inhibitor, such as Bortezomib, or hydroxyurea.

To "treat" a disease as the term is used herein, means to reduce the frequency or severity of at least one sign or symptom of a disease or disorder experienced by a subject. The compositions described above are typically administered to a subject in an effective amount, that is, an amount capable of producing a desirable result. The desirable result will depend upon the active agent being administered. For example, an effective amount of a rAAV particle may be an amount of the particle that is capable of transferring a heterologous nucleic acid to a host organ, tissue, or cell.

Toxicity and efficacy of the compositions utilized in methods of the disclosure can be determined by standard pharmaceutical procedures, using either cells in culture or experimental animals to determine the $LD_{50}$ (the dose lethal to 50% of the population). The dose ratio between toxicity and efficacy the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an $ED_{50}$ with little or no toxicity. The dosage may vary within this range depending upon the dosage form employed and the route of administration utilized.

Recombinant AAV (rAAV) Particles and Nucleic Acid Segments

Aspects of the disclosure relate to recombinant adeno-associated virus (rAAV) particles or preparations of such particles for delivery of one or more nucleic acid segments comprising a sequence encoding a protein or polypeptide of interest, into various tissues, organs, and/or cells. In some embodiments, the rAAV particle is delivered to a host cell as described herein.

The wild-type AAV genome is a single-stranded deoxyribonucleic acid (ssDNA), either positive- or negative-sensed. The genome comprises two inverted terminal repeats (ITRs), one at each end of the DNA strand, two open reading frames (ORFs): rep and cap between the ITRs, and an insert nucleic acid positioned between the ITRs and optionally comprising a transgene. The rep ORF comprises four overlapping genes encoding Rep proteins required for the AAV life cycle. The cap ORF comprises overlapping genes encoding capsid proteins: VP1, VP2 and VP3, which interact together to form the viral capsid. VP1, VP2 and VP3 are translated from one mRNA transcript, which can be spliced in two different manners: either a longer or shorter intron can be excised resulting in the formation of two isoforms of mRNAs: a ~2.3 kb- and a ~2.6 kb-long mRNA isoform. The capsid forms a supramolecular assembly of approximately 60 individual capsid protein subunits into a non-enveloped, T-1 icosahedral lattice capable of protecting the AAV genome. The mature capsid is composed of VP1, VP2, and VP3 (molecular masses of approximately 87, 73, and 62 kDa respectively) in a ratio of about 1:1:10.

Recombinant AAV (rAAV) particles may comprise a nucleic acid segment, which may comprise at a minimum: (a) one or more transgenes comprising a sequence encoding a protein or polypeptide of interest or an RNA of interest (e.g., a siRNA or microRNA) and (b) one or more regions comprising inverted terminal repeat (ITR) sequences (e.g., engineered ITR sequences) flanking the one or more nucleic acid regions (e.g., transgenes). In some embodiments, the nucleic acid segment is between 4 kb and 5 kb in size (e.g., 4.2 to 4.7 kb in size). Any nucleic acid segment described herein may be encapsidated by a viral capsid, such as an AAV6 capsid or another serotype (e.g., a serotype that is of the same serotype as the ITR sequences), which may comprises a modified capsid protein as described herein. In some embodiments, the nucleic acid segment is circular. In some embodiments, the nucleic acid segment is single-stranded.

In some embodiments, the nucleic acid segment is double-stranded. In some embodiments, a double-stranded nucleic acid segment may be, for example, a self-complementary vector that contains a region of the nucleic acid segment that is complementary to another region of the nucleic acid segment, initiating the formation of the double-strandedness of the nucleic acid segment.

Accordingly, in some embodiments, an rAAV particle or rAAV preparation containing such particles comprises a viral capsid and a nucleic acid segment as described herein, which is encapsidated by the viral capsid. In some embodiments, the insert nucleic acid of the nucleic acid segment comprises (1) one or more transgenes (e.g., a Factor IX or a Factor VIII gene) comprising a sequence encoding a protein or polypeptide of interest, (2) one or more nucleic acid regions comprising a sequence that facilitates expression of the transgene (e.g., a promoter), and (3) one or more nucleic acid regions comprising a sequence that facilitate integration of the transgene (optionally with the one or more nucleic acid regions comprising a sequence that facilitates expression) into the genome of the subject. In certain embodiments, the promoter of the insert nucleic acid comprises a sequence that has at least 90%, at least 95%, or at least 99% identity to a chicken β-actin (CBA) promoter. In some embodiments, the promoter comprises a nucleotide sequence that differs from the CBA promoter by 1, 2, 3, 4, 5, 6, 7, 8, 9, 10, 11, 12, 13, 14, 15, 16, 17, or 18 nucleotides.

In certain embodiments, the one or more miRNA sequences are operably controlled by a single promoter. In other embodiments, the one or more miRNA sequences are operably controlled by multiple promoters.

In some embodiments, the nucleic acid segment comprises one or more transgenes comprising a sequence encoding a protein or polypeptide of interest operably linked to a promoter, wherein the one or more transgenes are flanked on each side with an ITR sequence, and operably linked to a promoter (e.g., a CBA promoter). The ITR sequences can be derived from any AAV serotype (e.g., 1, 2, 3, 4, 5, 6, 7, 8, 9, or 10) or can be derived from more than one serotype. In some embodiments, the ITR sequences are derived from AAV2 or AAV6. In some embodiments, the ITR sequences of the first serotype are derived from AAV3, AAV2, AAV6 or AAV8. In other embodiments, the ITR sequences of the first serotype are derived from AAV1, AAV5, AAV8, AAV9 or AAV10. In some embodiments, the ITR sequences are the same serotype as the capsid (e.g., AAV3 ITR sequences and AAV3 capsid, etc.).

ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, et al. *Proc Natl Acad Sci USA.* 1996; 93(24):14082-7; and Curtis A. Machida, Methods in Molecular Medicine™. *Viral Vectors for Gene Therapy Methods and Protocols.* 10.1385/1-59259-304-6:201 Humana Press Inc. 2003: Chapter 10, Targeted Integration by Adeno-Associated Virus. Matthew D. Weitzman, Samuel M. Young Jr., Toni Cathomen and Richard Jude Samulski; U.S. Pat. Nos. 5,139, 941 and 5,962,313, all of which are incorporated herein by reference).

In some embodiments, the nucleic acid segment comprises a pTR-UF-11 plasmid backbone, which is a plasmid that contains AAV2 ITRs. This plasmid is commercially available from the American Type Culture Collection (ATCC MBA-331).

Exemplary ITR sequences are provided below.

```
AAV2:
                               (SEQ ID NO: 8)
TTGGCCACTCCCTCTCTGCGCGCTCGCTCGCTCACTGAGGCCGGGCGACC

AAAGGTCGCCCGACGCCCGGGCTTTGCCCGGGCGGCCTCAGTGAGCGAGC

GAGCGCGCAGAGAGGGAGTGGCCAACTCCATCACTAGGGGTTCCT

AAV3:
                               (SEQ ID NO: 9)
TTGGCCACTCCCTCTATGCGCACTCGCTCGCTCGGTGGGGCCTGGCGACC

AAAGGTCGCCAGACGGACGTGCTTTGCACGTCCGGCCCCACCGAGCGAGC

GAGTGCGCATAGAGGGAGTGGCCAACTCCATCACTAGAGGTATGGC

AAV6:
```

```
                              (SEQ ID NO: 10)
TTGCCCACTCCCTCTATGCGCGCTCGCTCGCTCGGTGGGGCCTGCGGACC

AAAGGTCCGCAGACGGCAGAGCTCTGCTCTGCCGGCCCCACCGAGCGAGC

GAGCGCGCATAGAGGGAGTGGGCAACTCCATCACTAGGGGTA

AAV5:
                              (SEQ ID NO: 11)
CTCTCCCCCCTGTCGCGTTCGCTCGCTCGCTGGCTCGTTTGGGGGGGTGG

CAGCTCAAAGAGCTGCCAGACGACGGCCCTCTGGCCGTCGCCCCCCCAAA

CGAGCCAGCGAGCGAGCGAACGCGACAGGGGGGAGAGTGCCACACTCTCA

AGCAAGGGGGTTTTGTA
```

The rAAV particle comprising a nucleic acid segment as described herein may be delivered in the form of a composition, such as a composition comprising the active ingredient, such as the rAAV particle, nucleic acid segment (in any form contemplated herein), and a therapeutically or pharmaceutically acceptable carrier. The rAAV particles or nucleic acid segment may be prepared in a variety of compositions, and may also be formulated in appropriate pharmaceutical vehicles for administration to human or animal subjects.

Other aspects of the disclosure are directed to methods that involve contacting cells with an rAAV preparation produced by a method described herein. The contacting may be, e.g., ex vivo or in vivo by administering the rAAV preparation to a subject. The rAAV particle or preparation may be delivered in the form of a composition, such as a composition comprising the active ingredient, such as a rAAV particle or preparation described herein, and a therapeutically or pharmaceutically acceptable excipient. The rAAV particles or preparations may be prepared in a variety of compositions, and may also be formulated in appropriate pharmaceutical vehicles for administration to human or animal subjects.

In some embodiments, the nucleic acid segment comprises one or more regions comprising a sequence that facilitates expression of the nucleic acid (e.g., the transgene), such as expression control sequences operatively linked to the nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer).

To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter.

Inducible promoters and/or regulatory elements may also be contemplated for achieving appropriate expression levels of the protein or polypeptide of interest. Non-limiting examples of suitable inducible promoters include the CBA promoter and those promoters from genes such as cytochrome P450 genes, heat shock protein genes, metallothionein genes, and hormone-inducible genes, such as the estrogen gene promoter.

Tissue-specific promoters and/or regulatory elements are also contemplated herein. Non-limiting examples of such promoters that may be used include species-specific promoters.

Synthetic promoters are also contemplated herein. A synthetic promoter may comprise, for example, regions of known promoters, regulatory elements, transcription factor binding sites, enhancer elements, repressor elements, and the like.

In some embodiments, a nucleic acid segment described herein may also contain marker or reporter genes, e.g., LacZ or a fluorescent protein such as luciferase.

In some embodiments, the nucleic acid segment comprises one or more transgenes comprising a sequence encoding a protein or polypeptide of interest, such as a therapeutic protein provided in Table 1 or described herein.

The transgene encoding the protein or polypeptide of interest may be, e.g., a polypeptide or protein of interest provided in Table 1. The sequences of the polypeptide or protein of interest may be obtained, e.g., using the non-limiting National Center for Biotechnology Information (NCBI) Protein IDs or SEQ ID NOs from patent applications provided in Table 1. In particular embodiments, the transgene is Factor IX (FIX), a clotting factor that useful in treatment of hemophilia A and/or hemophilia B patients. In some embodiments, the transgene is Factor IX, wild-type or Factor IX, Padua mutant.

TABLE 1

| | Non-limiting Exemplary diseases | Exemplary NCBI Protein IDs or Patent SEQ ID NOs |
|---|---|---|
| Protein or Polypeptide | | |
| acid alpha-glucosidase (GAA) | Pompe Disease | NP_000143.2, NP_001073271.1, NP_001073272.1 |
| Methyl CpG binding protein 2 (MECP2) | Rett syndrome | NP_001104262.1, NP_004983.1 |
| Aromatic L-amino acid decarboxylase (AADC) | Parkinson's disease | NP_000781.1, NP_001076440.1, NP_001229815.1, NP_001229816.1, NP_001229817.1, NP_001229818.1, NP_001229819.1 |
| Glial cell-derived neurotrophic factor (GDNF) | Parkinson's disease | NP_000505.1, NP_001177397.1, NP_001177398.1, NP_001265027.1, NP_954701.1 |
| Cystic fibrosis transmembrane conductance regulator (CFTR) | Cystic fibrosis | NP_000483.3 |
| Tumor necrosis factor receptor fused to an antibody Fc (TNFR:Fc) | Arthritis, Rheumatoid arthritis | SEQ ID NO. 1 of WO2013025079 |
| HIV-1 gag-proΔrt (tgAAC09) | HIV infection | SEQ ID NOs. 1-5 of WO2006073496 |
| Sarcoglycan alpha, beta, gamma, delta, epsilon, or zeta (SGCA, SGCB, SGCG, SGCD, SGCE, or SGCZ) | Muscular dystrophy | SGCA NP_000014.1, NP_001129169.1 SGCB NP_000223.1 SGCG NP_000222.1 SGCD NP_000328.2, NP_001121681.1, NP_758447.1 SGCE NP_001092870.1, NP_001092871.1, NP_003910.1 SGCZ NP_631906.2 |
| Alpha-1-antitrypsin (AAT) | Hereditary emphysema or Alpha-1-antitrypsin deficiency | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 |

TABLE 1-continued

Non-limiting examples of proteins or polypeptides of interest and associated diseases

| Protein or Polypeptide | Non-limiting Exemplary diseases | Exemplary NCBI Protein IDs or Patent SEQ ID NOs |
|---|---|---|
| Glutamate decarboxylase 1 (GAD1) | Parkinson's disease | NP_000808.2, NP_038473.2 |
| Glutamate decarboxylase 2 (GAD2) | Parkinson's disease | NP_000809.1, NP_001127838.1 |
| Aspartoacylase (ASPA) | Canavan's disease | NP_000040.1, NP_001121557.1 |
| Nerve growth factor (NGF) | Alzheimer's disease | NP_002497.2 |
| Granulocyte-macrophage colonystimulating factory (GM-CSF) | Prostate cancer | NP_000749.2 |
| Cluster of Differentiation 86 (CD86 or B7-2) | Malignant melanoma | NP_001193853.1, NP_001193854.1, NP_008820.3, NP_787058.4, NP_795711.1 |
| Interleukin 12 (IL-12) | Malignant melanoma | NP_000873.2, NP_002178.2 |
| neuropeptide Y (NPY) | Parkinson's disease, epilepsy | NP_000896.1 |
| ATPase, Ca++ transporting, cardiac muscle, slow twitch 2 (SERCA2) | Chronic heart failure | NP_001672.1, NP_733765.1 |
| Dystrophin or Minidystrophin | Muscular dystrophy | NP_000100.2, NP_003997.1, NP_004000.1, NP_004001.1, NP_004002.2, NP_004003.1, NP_004004.1, NP_004005.1, NP_004006.1, NP_004007.1, NP_004008.1, NP_004009.1, NP_004010.1, NP_004011.2, NP_004012.1, NP_004013.1, NP_004014.1 |
| Ceroid lipofuscinosis neuronal 2 (CLN2) | Late infantile neuronal ceroidlipofuscinosis or Batten's disease | NP_000382.3 |
| Neurturin (NRTN) | Parkinson's disease | NP_004549.1 |
| N-acetylgluco saminidase, alpha (NAGLU) | Sanfilippo syndrome (MPSIIIB) | NP_000254.2 |
| Iduronidase, alpha-1 (IDUA) | MPSI-Hurler | NP_000194.2 |
| Iduronate 2-sulfatase (IDS) | MPSII-Hunter | NP_000193.1, NP_001160022.1, NP_006114.1 |
| Glucuronidase, beta (GUSB) | MPSVII-Sly | NP_000172.2, NP_001271219.1 |
| Hexosaminidase A, α polypeptide (HEXA) | Tay-Sachs | NP_000511.2 |
| Retinal pigment epithelium- specific protein 65 kDa (RPE65) | Leber congenital amaurosis | NP_000320.1 |
| Factor IX (FIX) Factor IX, Padua mutant | Hemophilia B | NP_000124.1 |
| Adenine nucleotide translocator (ANT-1) | progressive external ophthalmoplegia | NP_001142.2 |
| ApaLI | mitochondrial heteroplasmy, myoclonic epilepsy with ragged red fibers (MERRF) or mitochondrial encephalomyopathy, lactic acidosis, and stroke- like episodes (MELAS) | YP_007161330.1 |
| NADH ubiquinone oxidoreductase subunit 4 (ND4) | Leber hereditary optic | YP_003024035.1 |
| very long-acyl-CoA dehydrogenase (VLCAD) | very long-chain acyl-CoA dehydrogenase (VLCAD) deficiency | NP_000009.1, NP_001029031.1, NP_001257376.1, NP_001257377.1 |
| short-chain acyl-CoA dehydrogenase (SCAD) | short-chain acyl-CoA dehydrogenase (SCAD) deficiency | NP_000008.1 |

TABLE 1-continued

Non-limiting examples of proteins or polypeptides of interest and associated diseases

| Protein or Polypeptide | Non-limiting Exemplary diseases | Exemplary NCBI Protein IDs or Patent SEQ ID NOs |
|---|---|---|
| medium-chain acyl-CoA dehydrogenase (MCAD) | medium-chain acyl-CoA dehydrogenase (MCAD) deficiency | NP_000007.1, NP_001120800.1, NP_001272971.1, NP_001272972.1, NP_001272973.1 |
| Myotubularin 1 (MTM1) | X-linked myotubular myopathy | NP_000243.1 |
| Myophosphorylase (PYGM) | McArdle disease (glycogen storage disease type V, myophosphorylase deficiency) | NP_001158188.1, NP_005600.1 |
| Lipoprotein lipase (LPL) | LPL deficiency | NP_000228.1 |
| sFLT01 (VEGF/PlGF (placental growth factor) binding domain of human VEGFR1/Flt-1 (hVEGFR1) fused to the Fc portion of human IgG(1) through a polyglycine linker) | Age-related macular degeneration | SEQ ID NOs: 2, 8, 21, 23, or 25 of WO 2009/105669 |
| Glucocerebrosidase (GC) | Gaucher disease | NP_000148.2, NP_001005741.1, NP_001005742.1, NP_001165282.1, NP_001165283.1 |
| UDP glucuronosyltransferase 1 family, polypeptide A1 (UGT1A1) | Crigler-Najjar syndrome | NP_000454.1 |
| Glucose 6-phosphatase (G6Pase) | GSD-Ia | NP_000142.2, NP_001257326.1 |
| Ornithine carbamoyltransferase (OTC) | OTC deficiency | NP_000522.3 |
| Cystathionine-beta-synthase (CBS) | Homocystinuria | NP_000062.1, NP_001171479.1, NP_001171480.1 |
| Factor VIII (F8) | Hemophilia A | NP_000123.1, NP_063916.1 |
| Hemochromatosis (HFE) | Hemochromatosis | NP_000401.1, NP_620572.1, NP_620573.1, NP_620575.1, NP_620576.1, NP_620577.1, NP_620578.1, NP_620579.1, NP_620580.1 |
| Low density lipoprotein receptor (LDLR) | Phenylketonuria (PKU) | NP_000518.1, NP_001182727.1, NP_001182728.1, NP_001182729.1, NP_001182732.1 |
| Galactosidase, alpha (AGA) | Fabry disease | NP_000160.1 |
| Phenylalanine hydroxylase (PAH) | Hypercholesterolaemia or Phenylketonuria (PKU) | NP_000268.1 |
| Propionyl CoA carboxylase, alpha polypeptide (PCCA) | Propionic acidaemias | NP_000273.2, NP_001121164.1, NP_001171475.1 |

Other exemplary polypeptides or proteins of interest include adrenergic agonists, anti-apoptosis factors, apoptosis inhibitors, cytokine receptors, cytokines, cytotoxins, erythropoietic agents, glutamic acid decarboxylases, glycoproteins, growth factors, growth factor receptors, hormones, hormone receptors, interferons, interleukins, interleukin receptors, kinases, kinase inhibitors, nerve growth factors, netrins, neuroactive peptides, neuroactive peptide receptors, neurogenic factors, neurogenic factor receptors, neuropilins, neurotrophic factors, neurotrophins, neurotrophin receptors, N-methyl-D-aspartate antagonists, plexins, proteases, protease inhibitors, protein decarboxylases, protein kinases, protein kinases inhibitors, proteolytic proteins, proteolytic protein inhibitors, semaphoring, semaphorin receptors, serotonin transport proteins, serotonin uptake inhibitors, serotonin receptors, serpins, serpin receptors, and tumor suppressors. In some embodiments, the polypeptide or protein of interest is a human protein or polypeptide.

The rAAV particle or particle within an rAAV preparation may be of any AAV serotype, including any derivative or pseudotype (e.g., 1, 2, 3, 4, 5, 6, 7, 8, 9, 10, 2/1, 2/5, 2/8, 2/9, 3/1, 3/5, 3/8, or 3/9). As used herein, the serotype of an rAAV viral vector (e.g., an rAAV particle) refers to the serotype of the capsid proteins of the recombinant virus. In some embodiments, the capsid protein of the rAAV particle is AAV3, AAV2, AAV6 or AAV8, or a variant thereof. In other embodiments, the capsid protein of the rAAV particle is AAV1, AAV5, AAV9, AAV10, or a variant thereof. In some embodiments, the rAAV particle is not AAV2. In some embodiments, the rAAV particle is not AAV8.

Non-limiting examples of derivatives and pseudotypes include rAAV2/1, rAAV2/5, rAAV2/8, rAAV2/9, AAV2-

AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., *Mol Ther.* 2012 Apr. 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid segment comprising ITRs from one serotype (e.g., AAV2, AAV3) and (b) a capsid comprised of capsid proteins derived from another serotype (e.g., AAV1, AAV2, AAV3, AAV4, AAV5, AAV6, AAV7, AAV8, AAV9, or AAV10). Methods for producing and using pseudotyped rAAV vectors are known in the art (see, e.g., Duan et al., *J. Virol.*, 75:7662-7671, 2001; Halbert et al., *J. Virol.*, 74:1524-1532, 2000; Zolotukhin et al., *Methods*, 28:158-167, 2002; and Auricchio et al., *Hum. Molec. Genet.*, 10:3075-3081, 2001).

In some embodiments, the rAAV particle comprises a capsid that includes modified capsid proteins (e.g., capsid proteins comprising a modified VP3 region). Methods of producing modified capsid proteins are known in the art (see, e.g., US Patent Publication No. 2013/0310443, which is incorporated herein by reference in its entirety). In some embodiments, the rAAV particle comprises a modified capsid protein comprising a non-tyrosine residue (e.g., a phenylalanine) at a position that corresponds to a surface-exposed tyrosine residue in a wild-type capsid protein, a non-threonine residue (e.g., a valine) at a position that corresponds to a surface-exposed threonine residue in the wild-type capsid protein, a non-lysine residue (e.g., a glutamic acid) at a position that corresponds to a surface-exposed lysine residue in the wild-type capsid protein, a non-serine residue (e.g., valine) at a position that corresponds to a surface-exposed serine residue in the wild-type capsid protein, or a combination thereof. Exemplary surface-exposed lysine residues include positions that correspond to K258, K321, K459, K490, K507, K527, K532, K544, K549, K556, K649, K655, K665, or K706 of the wild-type AAV2 capsid protein. Exemplary surface-exposed serine residues include positions that correspond to S261, S264, S267, S276, S384, S458, S468, S492, S498, S578, S658, S662, S668, S707, or S721 of the wild-type AAV2 capsid protein. Exemplary surface-exposed threonine residues include positions that correspond to T251, T329, T330, T454, T455, T503, T550, T592, T581, T597, T491, T671, T659, T660, T701, T713, or T716 of the wild-type AAV2 capsid protein. Exemplary surface-exposed tyrosine residues include positions that correspond to Y252, Y272, Y444, Y500, Y700, Y704, or Y730 of the wild-type AAV2 capsid protein.

In some embodiments, the modified capsid protein comprises a non-tyrosine (e.g., a phenylalanine) residue at one or more of or each of Y705 and Y731 of a wild-type AAV3 capsid protein. In some embodiments, the modified capsid protein comprises a non-serine residue (e.g., valine) and/or a non-threonine residue (e.g., valine) at one or more of or each of S663 and T492 of a wild-type AAV3 capsid protein. In some embodiments, the modified capsid protein comprises a non-serine residue (e.g., valine), a non-threonine residue (e.g., valine), and/or a non-lysine residue (e.g., arginine) at one or more of or each of S663, T492V and K533 of a wild-type AAV3 capsid protein. In some embodiments, the modified capsid protein comprises a non-tyrosine (e.g., a phenylalanine) residue, non-serine residue (e.g., valine), a non-threonine residue (e.g., valine), and/or a non-lysine residue (e.g., arginine) at one or more of or each of Y705, Y731, S663, T492V and K533 of a wild-type AAV3 capsid protein.

In other embodiments, the modified capsid protein comprises a non-native amino acid substitution at amino acid residue 533 of a wild-type AAV8 capsid, wherein the non-native amino acid substitution is E533K, Y733F, or a combination thereof. The AAV8(Y733F) capsid is described in Doroudchi et al., *Amer. Soc. of Gene & Cell Ther.* 19(7): 1220-29 (2011), herein incorporated by reference. In certain embodiments, the modified capsid comprises AAV7BP2, a variant of AAV8.

In some embodiments, the modified capsid protein comprises a non-tyrosine residue and/or a non-threonine residue at one or more of or each of Y705, Y731, and T492 of a wild-type AAV6 capsid protein (see sequence below with Y705, Y731, and T492 positions *emphasized*). In some embodiments, the non-tyrosine residue is phenylalanine and the non-threonine residue is valine:

```
                                        (SEQ ID NO: 12)
  1  MAADGYLPDW  LEDNLSEGIR  EWWDLKPGAP  KPKANQQKQD

DGRGLVLPGY

51  KYLGPFNGLD  KGEPVNAADA  AALEHDKAYD  QQLKAGDNPY

LRYNHADAEF

101  QERLQEDTSF  GGNLGRAVFQ  AKKRVLEPFG  LVEEGAKTAP

GKKRPVEQSP

151  QEPDSSSGIG  KTGQQPAKKR  LNFGQTGDSE  SVPDPQPLGE

PPATPAAVGP

201  TTMASGGGAP  MADNNEGADG  VGNASGNWHC  DSTWLGDRVI

TTSTRTWALP

251  TYNNHLYKQI  SSASTGASND  NHYFGYSTPW  GYFDFNRFHC

HFSPRDWQRL

301  INNNWGFRPK  RLNFKLFNIQ  VKEVTTNDGV  TTIANNLTST

VQVFSDSEYQ

351  LPYVLGSAHQ  GCLPPFPADV  FMIPQYGYLT  LNNGSQAVGR

SSFYCLEYFP

401  SQMLRTGNNF  TFSYTFEDVP  FHSSYAHSQS  LDRLMNPLID

QYLYFLNRTQ

451  NQSGSAQNKD  LLFSRGSPAG  MSVQPKNWLP  GPCYRQQRVS

KᴵKTDNNNSN

501  FTWTGASKYN  LNGRESIINP  GTAMASHKDD  KDKFFPMSGV

MIFGKESAGA

551  SNTALDNVMI  TDEEEIKATN  PVATERFGTV  AVNLQSSSTD

PATGDVHVMG
```

25

```
                         -continued
601  ALPGMVWQDR DVYLQGPIWA KIPHTDGHFH PSPLMGGFGL

KHPPPQILIK

651  NTPVPANPPA EFSATKFASF ITQYSTGQVS VEIEWELQKE

NSKRWNPEVQ

701  YTSNᴸAKSAN VDFTVDNNGL YTEPRPIGTR ᴸLTRPL
```

In some embodiments, two rAAV particles are contemplated. In some embodiments, the first rAAV particle comprises a nucleic acid segment as described herein (e.g., comprising a one or more transgenes comprising a sequence encoding a protein or polypeptide of interest flanked by ITR sequences), and the second rAAV particle comprises a second nucleic acid segment that encodes a miRNA, e.g. miRNA 17-92 cluster.

Other aspects of the disclosure relate to a nucleic acid segment, such as a recombinant nucleic acid segment as described herein. In some embodiments, the nucleic acid segment comprises the one or more transgenes comprising a sequence encoding a protein or polypeptide of interest wherein the one or more transgenes are flanked by ITR sequences. In some embodiments, the nucleic acid segment is provided in a form suitable for inclusion in a rAAV particle, such as a single-stranded or self-complementary nucleic acid. In some embodiments, the nucleic acid segment is provided in a form suitable for use in a method of producing rAAV particles. For example, in some embodiments, the nucleic acid segment is a plasmid (e.g., comprising an origin of replication (such as an *E. coli* ORI) and optionally a selectable marker (such as an Ampicillin or Kanamycin selectable marker)).

Production Methods

Methods of producing rAAV particles and nucleic acid segments are described herein. Other methods are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Nos. US 2007/0015238 and US 2012/0322861, which are incorporated herein by reference; and plasmids and kits available from ATCC and Cell Biolabs, Inc.). For example, a plasmid containing the nucleic acid segment may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

In some embodiments, the one or more helper plasmids include a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV3, AAV5, or AAV6 and the cap gene is derived from AAV2, AAV3, AAV5, or AAV6 and may include modifications to the gene in order to produce the modified capsid protein described herein. In some embodiments, the rep gene is a rep gene derived from AAV2 or AAV6 and the cap gene is derived from AAV6 and may include modifications to the gene in order to produce the modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8. ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, *Human Gene Therapy*, Vol. 9, 2745-2760; Kern, A. et al. (2003), Identification of a Heparin-Binding Motif on Adeno-Associated Virus Type 2 Capsids, *Journal of Virology*, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, *Journal of Virology*, Vol. 79, 5296-5303; and Moullier, P. and Snyder, R. O. (2008), International efforts for recombinant adeno-associated viral vector reference standards, *Molecular Therapy*, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes for a first serotype (e.g., AAV3, AAV5, and AAV6), cap genes (which may or may not be of the first serotype) and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO₄-mediated transfection, lipids or polymeric molecules such as Polyethylenimine (PEI) with the helper plasmid(s) and a plasmid containing a nucleic acid segment described herein. The HEK293 cells are then incubated for at least 60 hours to allow for rAAV particle production. Alternatively, in another example Sf9-based producer stable cell lines are infected with a single recombinant baculovirus containing the nucleic acid segment. As a further alternative, in another example HEK293 or BHK cell lines are infected with a HSV containing the nucleic acid segment and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

Host Cells

The disclosure also contemplates host cells that comprise at least one of the disclosed rAAV particles or nucleic acid segments described herein. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

The disclosure also contemplates host cells that comprise at least one of the disclosed rAAV particles or nucleic acid segments. Such host cells include mammalian host cells, with human host cells being preferred, and may be either isolated, in cell or tissue culture. In the case of genetically modified animal models (e.g., a mouse), the transformed host cells may be comprised within the body of a non-human animal itself. In some embodiments, the host cell is a cancer cell. In some embodiments, the host cell is a liver cell, such as a liver cancer cell.

In certain embodiments, the host cells are HEK293 cells or HeLa cells.

In some embodiments, a host cell as described herein is derived from a subject as described herein. Host cells may be derived using any method known in the art, e.g., by isolating cells from a fluid or tissue of the subject. In some embodiments, the host cells are cultured. Methods for isolating and culturing cells are well known in the art.

Subjects

Aspects of the disclosure relate to methods and preparations for use with a subject, such as human or non-human primate subjects, a host cell in situ in a subject, or a host cell derived from a subject. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters.

In some embodiments, the subject has or is suspected of having a disease that may be treated with gene therapy. In some embodiments, the subject has or is suspected of having a hemoglobinopathy. A hemoglobinopathy is a disease characterized by one or more mutation(s) in the genome that results in abnormal structure of one or more of the globin chains of the hemoglobin molecule. Exemplary hemoglobinopathies include hemolytic anemia, sickle cell disease, and thalassemia. Sickle cell disease is characterized by the presence of abnormal, sickle-chalped hemoglobins, which can result in severe infections, severe pain, stroke, and an increased risk of death. Subjects having sickle cell disease can be identified, e.g., using one or more of a complete blood count, a blood film, hemoglobin electrophoresis, and genetic testing. Thalassemias are a group of autosomal recessive diseases characterized by a reduction in the amount of hemoglobin produced. Symptoms include iron overload, infection, bone deformities, enlarged spleen, and cardiac disease. The subgroups of thalassemias include alpha-thalassemia, beta-thalassemia, and delta thalassemia. Subjects having a thalassemia may be identified, e.g., using one or more of complete blood count, hemoglobin electrophoresis, Fe Binding Capacity, urine urobilin and urobilogen, peripheral blood smear, hematocrit, and genetic testing.

In some embodiments, the subject has or is suspected of having a disease that may be treated with gene therapy. In some embodiments, the subject has or is suspected of having a disease provided in Table 1.

In some embodiments, the subject has or is suspected of having a disease that may be treated with gene therapy. In some embodiments, the subject has or is suspected of having a proliferative disease, such as cancer. The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, the cancer is liver cancer. Exemplary liver cancers include, but are not limited to, hepatocellular carcinoma (HCC), cholangiocarcinoma, angiosarcoma, and hepatoblastoma. Subject having cancer can be identified by the skilled medical practitioner, e.g., using methods known in the art including biopsy, cytology, histology, endoscopy, X-ray, Magnetic Resonance Imaging (MRI), ultrasound, CAT scan (computerized axial tomography), genetic testing, and tests for detection of tumor antigens in the blood or urine.

Plasmid DNA-mediated transfection of miRNA 17-92 cluster leads to a significant increase in transgene expression from scAAV2 vectors. In the following Examples, the role of miR17-92 in AAV2 vector-mediated transgene expression was systematically evaluated. Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

In a first set of experiments, the transduction effects of dose-dependent administration of a plasmid encoding the miR17-92 cluster with an AAV2-encoded reporter gene was evaluated.

HeLa cells were transduced with self-complementary AAV2 particles expressing the mCherry reporter gene at a dose of 500 vgs/cell, in the presence of increasing amounts (0, 0.1, 0.3, or 0.5 µg) of a plasmid containing the miR17-92 cluster. Both mCherry reporter and miR17-92 cluster were operably controlled by chicken β-actin (CBA) promoters. A mock-infection formulation (PBS) was used as a negative control.

Figure 3A:
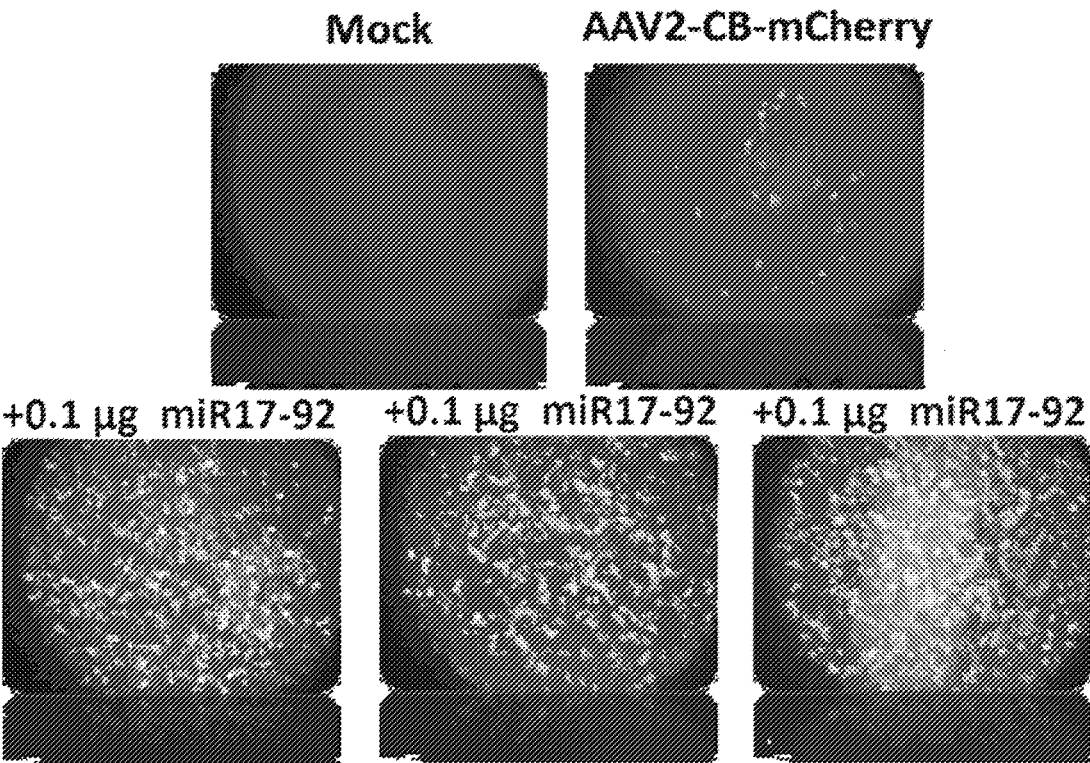
FIGS. 3A-3B illustrate the effects of miRNA 17-92 co-expression on the transduction efficiency of scAAV2-mCherry vectors.
Figure 3B:
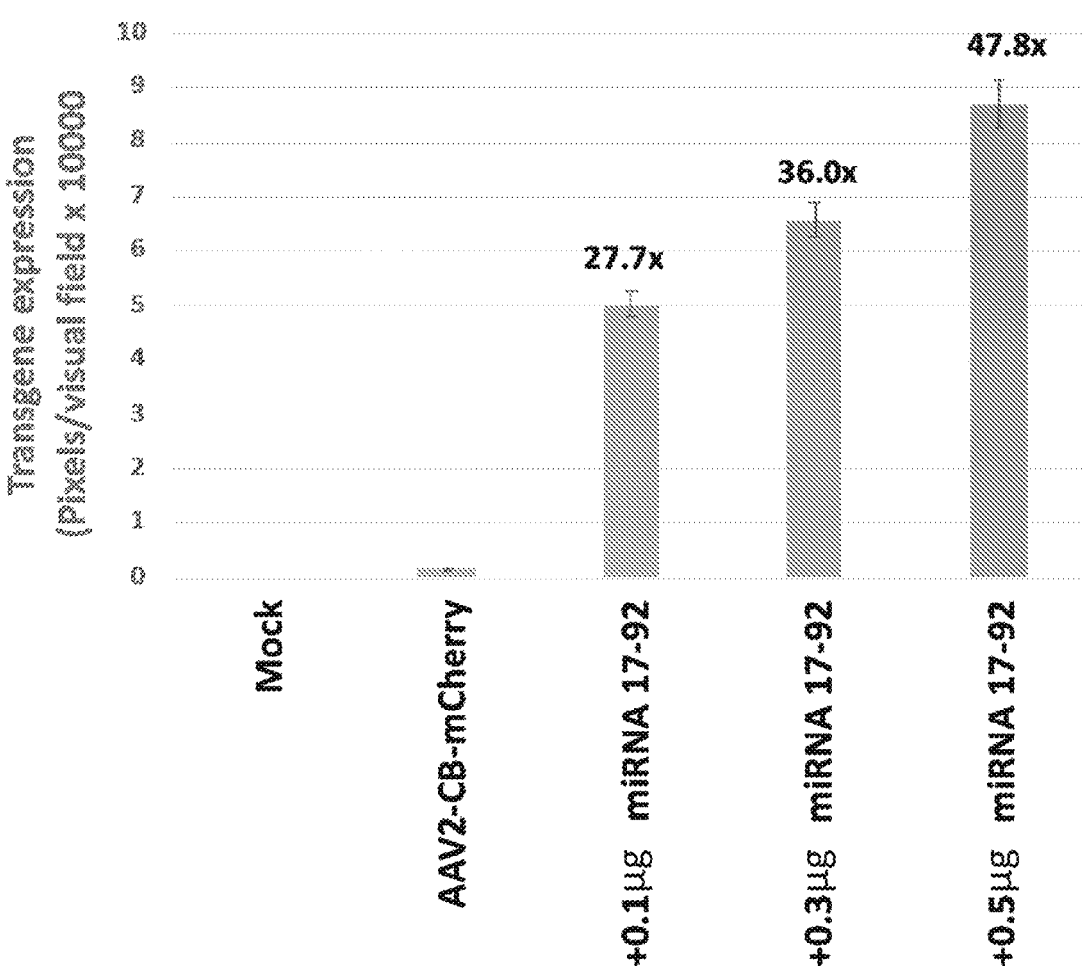

A dose-dependent increase in mCherry expression in the cells was evident with increasing amounts of the miR17-92 plasmid, suggesting that miR17-92-mediated GR activation led to the observed increase in mCherry expression (FIGS. 3A-3B). At the highest dose (0.5 µg) of miR17-92-expressing plasmid, mCherry expression was increased by a factor of 48 relative to the absence of plasmid.

Figure 4A:
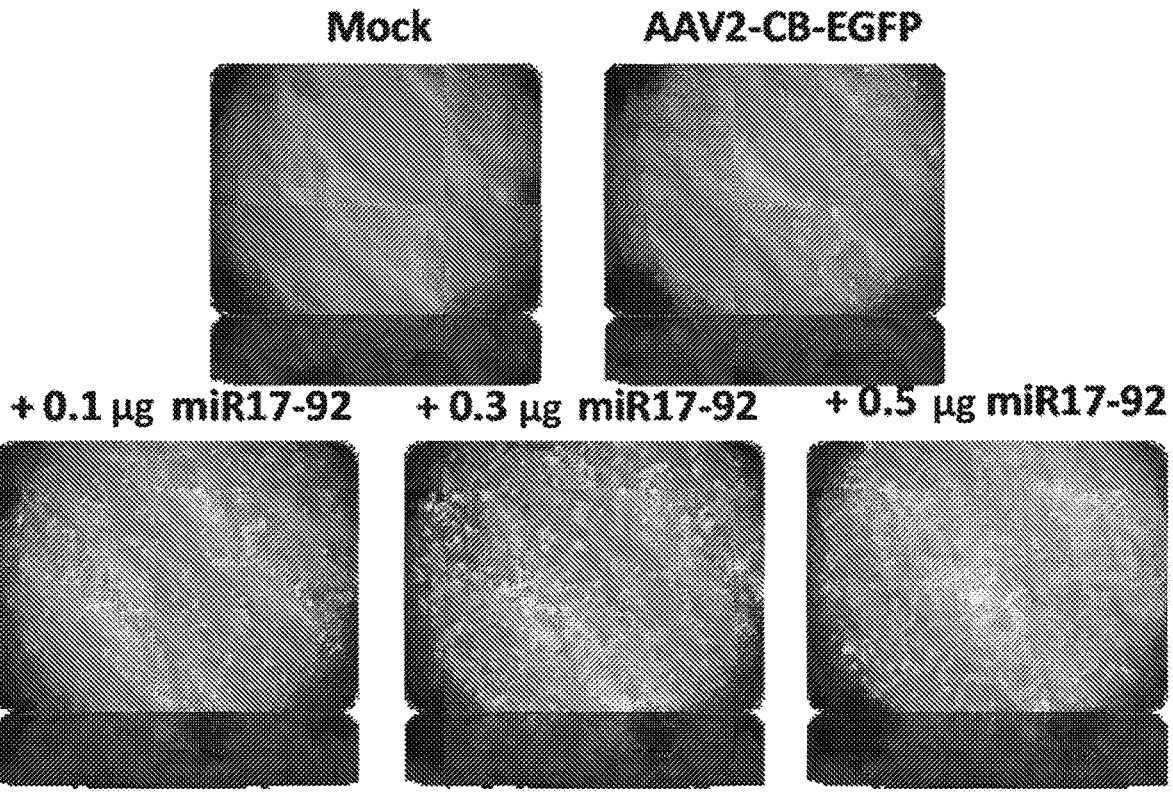
FIGS. 4A-4B illustrate the effects of miRNA 17-92 co-expression on the transduction efficiency of scAAV2-EGFP vectors.
Figure 4B:
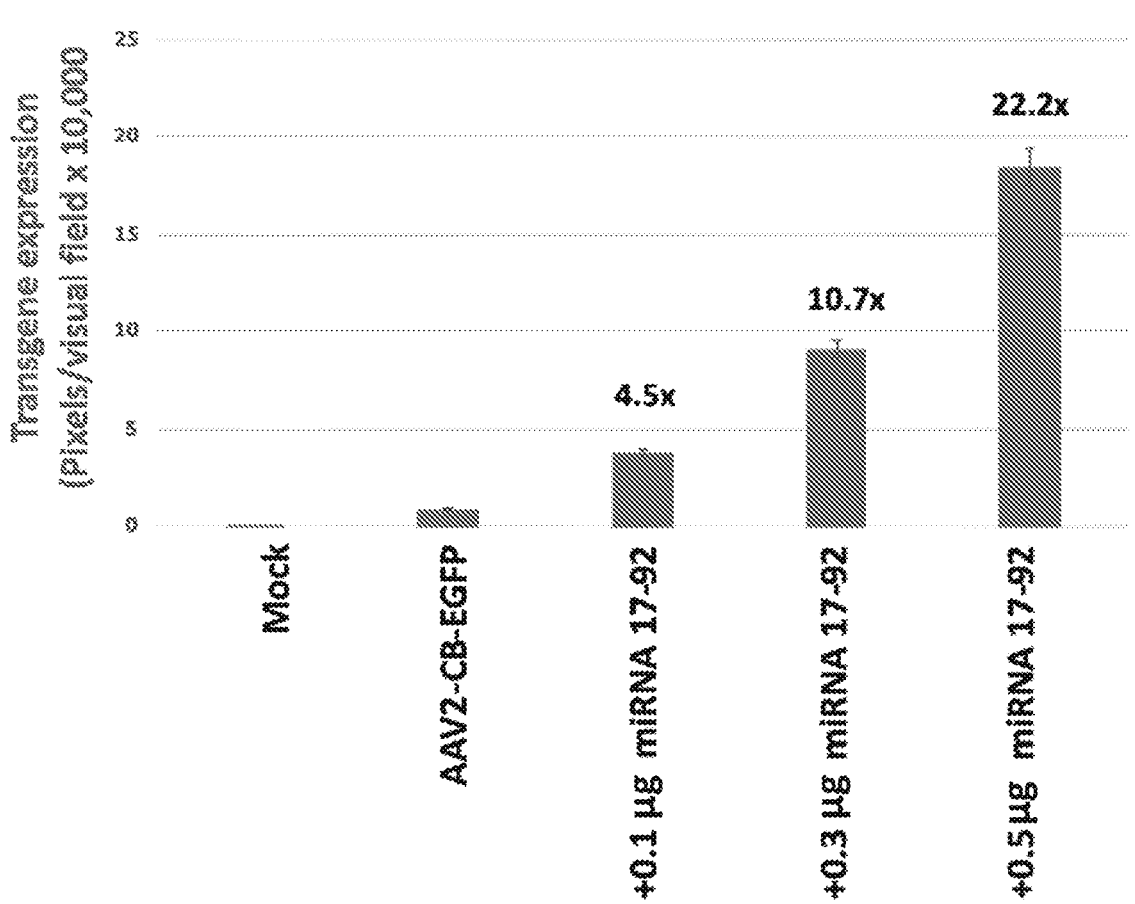

This experiment was repeated with scAAV2 vectors expressing the EGFP reporter gene under the control of a CBA promoter (FIGS. 4A-4B). At the highest dose (0.5 µg) of miR17-92-expressing plasmid, EGFP expression was increased by a factor of 22 relative to the absence of plasmid.

Example 2

The transduction effects of co-administration of ssAAV2 and scAAV2 vectors expressing miR17-92 with an AAV2-encoded reporter gene was evaluated.

Figure 5A:
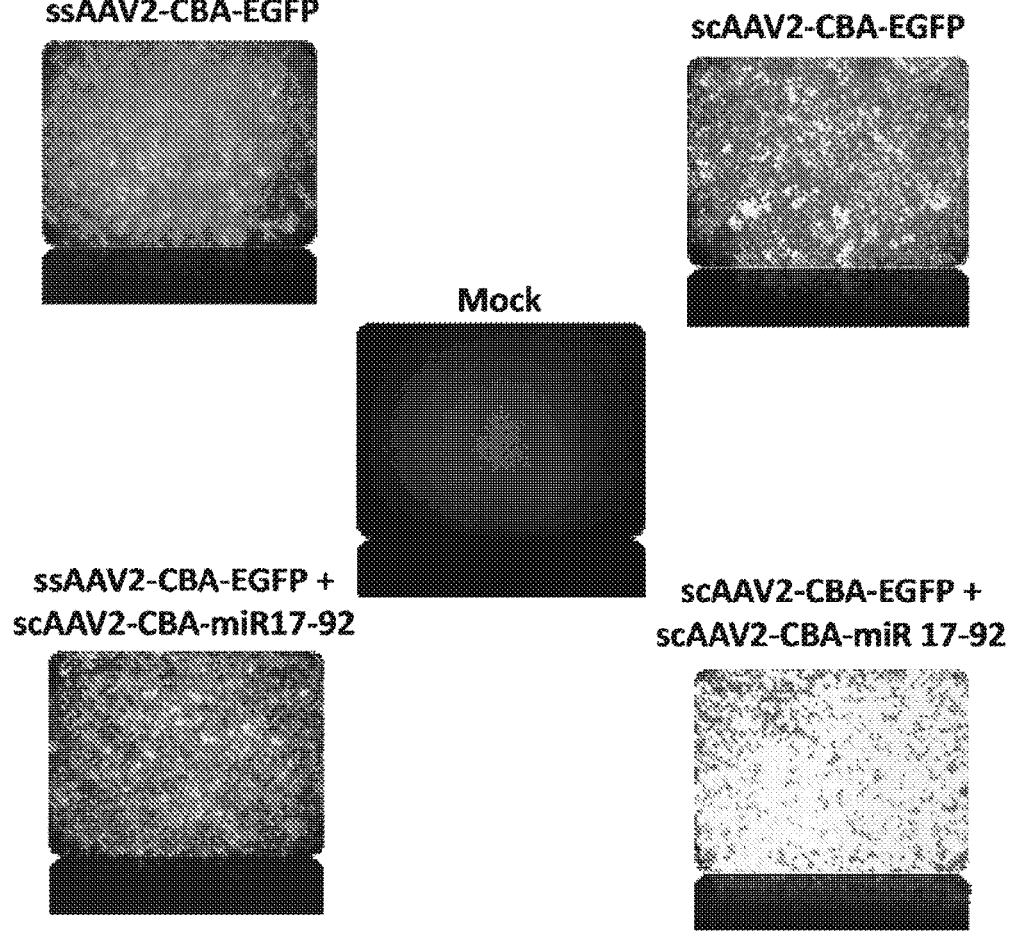
FIGS. 5A-5B illustrate the effect of co-transduction with scAAV2-miRNA 17-92 vectors on the transduction efficiency of ssAAV2-EGFP and scAAV2-EGFP vectors in trans.

Recombinant particles containing ssAAV2 and scAAV2 vectors expressing miR17-92 were generated (GenScript). HeLa cells were transduced with either ssAAV2 or scAAV2 vectors (at a dose of 500 vector genome copies (vgs) per cell each) expressing the EGFP reporter gene, either alone or co-transduced with scAAV2-miR17-92 vectors (5,000 vgs/cell each) (FIG. 5A). Thus, the ratio of miR17-92 vector to EGFP vector in both cases was 10:1. The EGFP transgene and miR17-92 cluster were operably controlled by CBA promoters. A mock-infection formulation (PBS) was used as a negative control.

Figure 5B:
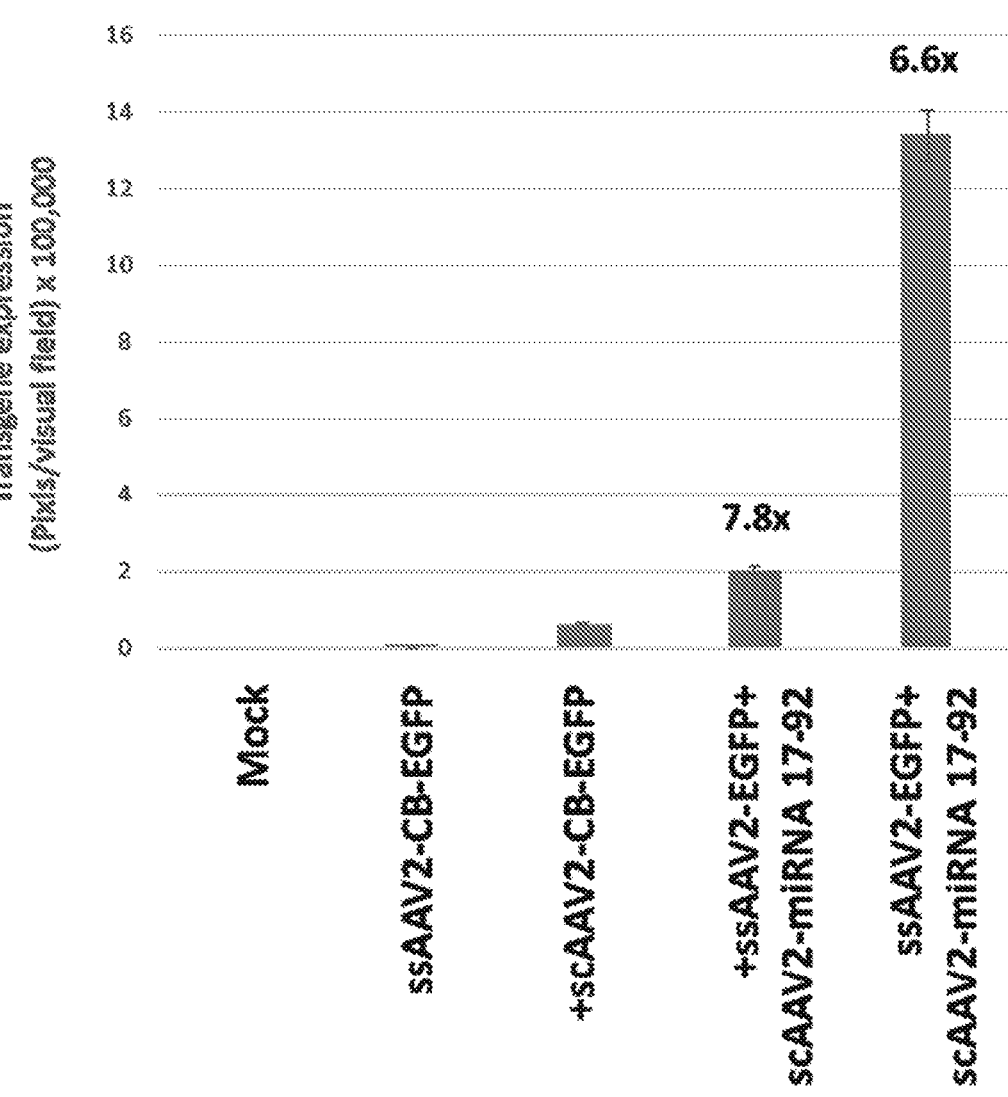

When co-administered with scAAV2-miR17-92, EGFP expression increased by about 7-fold for both scAAV2-EGFP and ssAAV2-EGFP (FIG. 5B).

Example 3

It was sought to determine whether similar enhanced transduction would be observed when the reporter and miR17-92 cluster were expressed in the same vector genome, or expression in cis.

Figure 6A:
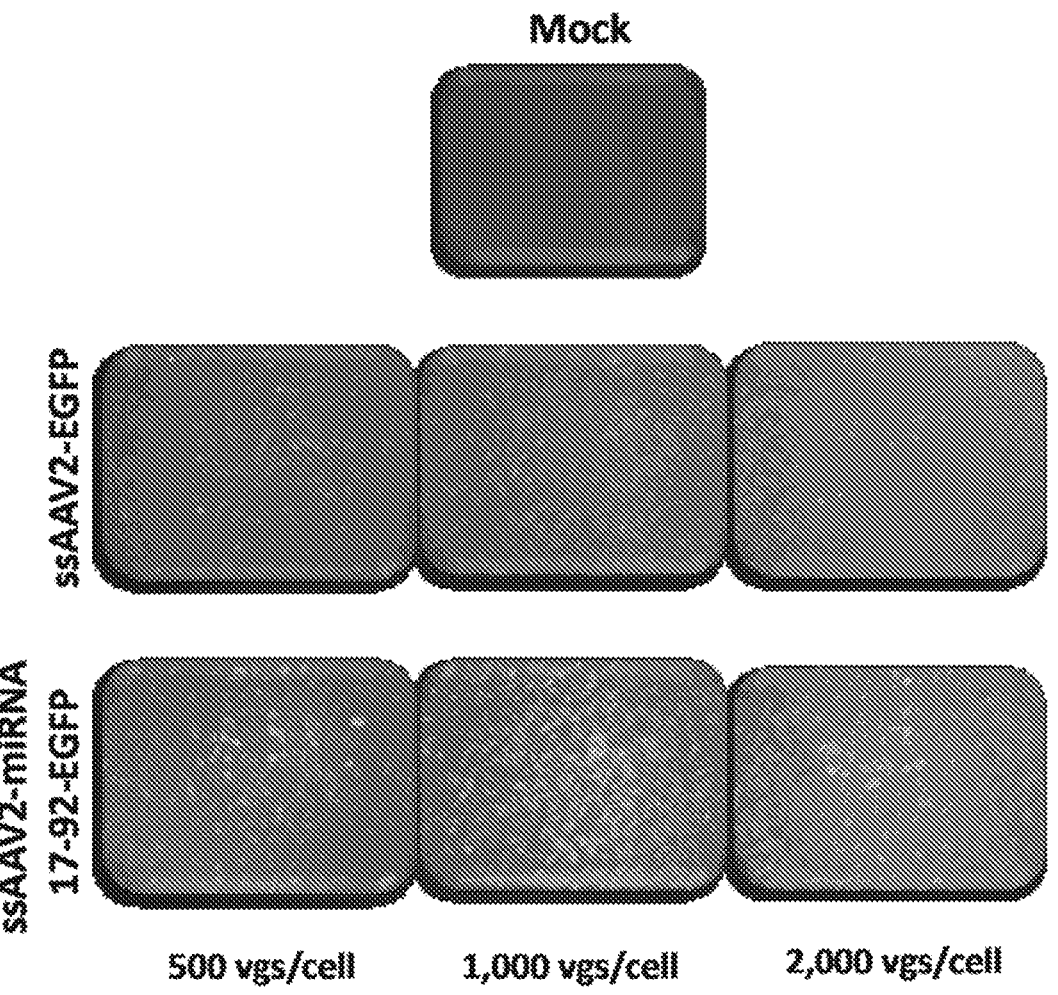
FIGS. 6A-6B illustrate the effect of miRNA 17-92 expression in cis on the transduction efficiency of ssAAV2 vectors.

The transduction efficiencies of ssAAV2-EGFP vectors, in the presence and absence of an miR17-92 cluster inserted into the same genome, were analyzed following transduction of HeLa cells at various doses (500, 1,000 and 2,000 vgs/cell) (FIG. 6A). The EGFP and miRNA cluster were operably controlled by a single CBA promoter.

Figure 6B:
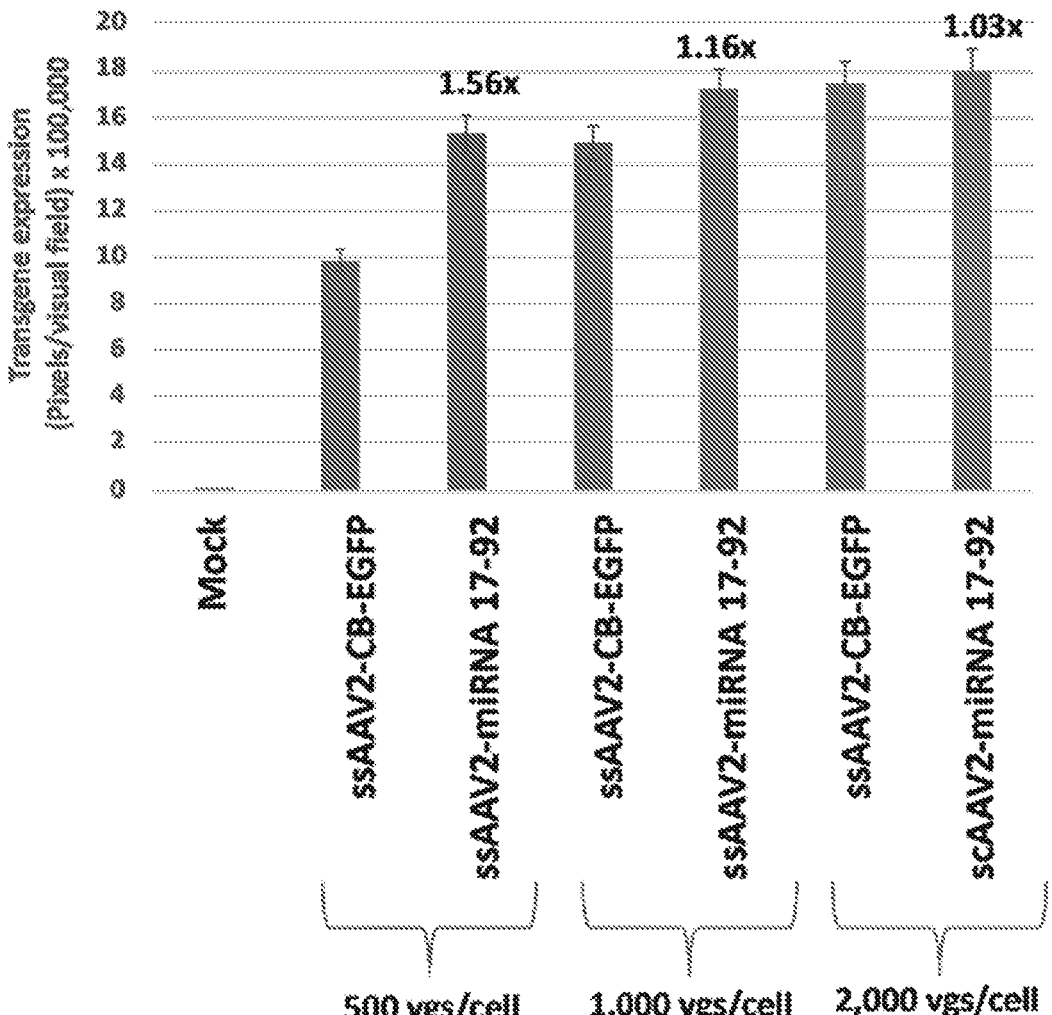

In each experiment, the presence in cis of the miR17-92 cluster led to about 2-fold increase in EGFP expression (FIG. 6B).

Taken together, these data suggest that co-administration of an ssAAV genome expressing the miR17-92 cluster gene is an attractive strategy to achieve improved transgene expression. For instance, this strategy may be applied to AAV-hF.IX vectors, such as ssAAV3-hF.IX vectors, ssAAV8-hF.IX vectors and scAAV8-hF.Ix vectors. Also, this strategy may be applied to AAV-hF.VIII vectors, such as ssAAV3-hF.VIII vectors, ssAAV8-hF.VIII vectors and scAAV8-hF.VIII vectors. These vectors could be used in gene therapies targeting hemophilia A or hemophilia B in humans. Co-administration in cis or in trans leads to enhanced transduction efficiencies, with trans expression resulting in more significant enhancement of expression.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

---

What is claimed is:

1. A composition comprising:
  a) a first rAAV nucleic acid comprising a heterologous nucleic acid encoding two or more miRNA sequences that activate glucocorticoid receptor (GR) activity, wherein the two or more miRNA sequences are selected from SEQ ID NOs: 1-6 and 13-16; and
  b) a second rAAV nucleic acid comprising a heterologous nucleic acid encoding a transgene of interest.

2. The composition of claim 1, wherein the first rAAV nucleic acid and the second rAAV nucleic acid are single-stranded.

3. The composition of claim 1, wherein the two or more miRNA sequences comprise a first sequence comprising SEQ ID NO: 1 and a second sequence comprising SEQ ID NO: 2.

4. The composition of claim 1, wherein the first rAAV nucleic acid is encapsidated within a first rAAV particle and the second rAAV nucleic acid is encapsidated within a second rAAV particle.

5. The composition of claim 1 further comprising a tyrphostin.

6. A method comprising contacting the composition of claim 1 with a cell.

7. The method of claim 6, wherein the cell is a mammalian cell.

8. The method of claim 7, wherein the mammalian cell is a human cell.

9. A method comprising administering the composition of claim 1 to a subject.

10. The method of claim 9, wherein the subject is a mammalian subject.

11. The method of claim 10, wherein the mammalian subject is a human.

* * * * *